United States Patent
Thomas et al.

(10) Patent No.: US 8,796,333 B2
(45) Date of Patent: *Aug. 5, 2014

(54) METHOD OF USING β-HYDROXY-β-METHYLBUTYRATE TO TREAT A CONDITION

(75) Inventors: Debra L. Thomas, Columbus, OH (US); Pradip Mukerji, Gahanna, OH (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/347,750

(22) Filed: Jan. 11, 2012

(65) Prior Publication Data

US 2012/0189709 A1    Jul. 26, 2012

Related U.S. Application Data

(62) Division of application No. 11/641,978, filed on Dec. 19, 2006.

(60) Provisional application No. 60/752,253, filed on Dec. 19, 2005.

(51) Int. Cl.
*A61K 31/191* (2006.01)
*A61K 31/19* (2006.01)

(52) U.S. Cl.
CPC ............... *A61K 31/19* (2013.01); *Y10S 514/826* (2013.01); *Y10S 514/885* (2013.01)
USPC ............................. 514/557; 514/826; 514/885

(58) Field of Classification Search
None
See application file for complete search history.

(56) References Cited

U.S. PATENT DOCUMENTS

| | | |
|---|---|---|
| 3,408,210 A | 10/1968 | Heyman |
| 3,542,560 A | 11/1970 | Tomarelli et al. |
| 4,104,290 A | 8/1978 | Koslowsky |
| 4,259,358 A | 3/1981 | Duthie |
| 4,742,081 A | 5/1988 | Stracher et al. |
| 4,866,040 A | 9/1989 | Stracher et al. |
| 4,992,470 A | 2/1991 | Nissen |
| 5,000,975 A | 3/1991 | Tomarelli |
| 5,028,440 A | 7/1991 | Nissen |
| 5,087,472 A | 2/1992 | Nissen |
| 5,167,957 A | 12/1992 | Webb, Jr. et al. |
| 5,171,442 A | 12/1992 | Nakshbendi |
| 5,223,285 A | 6/1993 | DeMichele et al. |
| 5,348,979 A | 9/1994 | Nissen et al. |
| 5,360,613 A | 11/1994 | Nissen |
| 5,431,928 A | 7/1995 | Saito et al. |
| 5,444,054 A | 8/1995 | Garleb et al. |
| 5,447,732 A | 9/1995 | Tanimoto et al. |
| 5,457,130 A | 10/1995 | Tisdale et al. |
| 5,601,860 A | 2/1997 | Lien et al. |
| 5,641,531 A | 6/1997 | Liebrecht et al. |
| 5,726,146 A | 3/1998 | Almada et al. |
| 5,780,451 A | 7/1998 | DeMichele et al. |
| 5,834,427 A | 11/1998 | Han et al. |
| 5,976,550 A | 11/1999 | Engel et al. |
| 6,031,000 A | 2/2000 | Nissen et al. |
| 6,060,446 A | 5/2000 | Zaloga et al. |
| 6,080,788 A | 6/2000 | Sole et al. |
| 6,103,764 A | 8/2000 | Nissen |
| 6,248,909 B1 | 6/2001 | Akimoto et al. |
| 6,291,525 B1 | 9/2001 | Nissen |
| 6,294,206 B1 | 9/2001 | Barrett-Reis et al. |
| 6,340,491 B1 | 1/2002 | Cain et al. |
| 6,420,342 B1 | 7/2002 | Hageman et al. |
| 6,468,987 B1 | 10/2002 | Demichele et al. |
| 6,475,539 B1 | 11/2002 | Dewille et al. |
| 6,521,591 B1 | 2/2003 | Smeets et al. |
| 6,596,767 B2 | 7/2003 | Masor et al. |
| 6,620,427 B2 | 9/2003 | Lasekan et al. |
| 6,660,258 B1 | 12/2003 | Tovey |
| 6,749,881 B2 | 6/2004 | Kataoka et al. |
| 7,332,178 B2 | 2/2008 | Byard et al. |
| 7,419,596 B2 | 9/2008 | Dueppen et al. |
| 7,435,442 B2 | 10/2008 | Servotte |

(Continued)

FOREIGN PATENT DOCUMENTS

| | | |
|---|---|---|
| CA | 2632262 A1 | 7/2007 |
| CN | 101785566 | 7/2010 |

(Continued)

OTHER PUBLICATIONS

MedicineNet, "Cancer", 2008, downloaded on Apr. 7, 2008 from http://www.medterms.com, 2 pages.*

(Continued)

*Primary Examiner* — Savitha Rao
*Assistant Examiner* — Gregg Polansky
(74) *Attorney, Agent, or Firm* — Calfee, Halter & Griswold LLP

(57) ABSTRACT

Disclosed are methods of treating an individual having a condition characterized by an imbalance in type 1 and type 2 cytokine production, wherein the method comprises administering to the individual an amount of β-hydroxy-β-methylbutyrate (HMB) effective to modulate or otherwise cause an increase in the ratio of type 1 to type 2 cytokines, including an increase in the ratio of type 1 to type 2 cytokines without a corresponding increase in type 2 cytokine levels. Also disclosed are methods of using HMB to treat asthma and allergies. The methods of the present invention are based upon the discovery that HMB modulates cytokine production, most typically by increasing type 1 cytokines without a corresponding increase in type 2 cytokines.

19 Claims, 5 Drawing Sheets

(56) References Cited

U.S. PATENT DOCUMENTS

| | | |
|---|---|---|
| 7,445,807 B2 | 11/2008 | Lockwood |
| 7,498,026 B2 | 3/2009 | Dahlqvist et al. |
| 7,517,850 B2 | 4/2009 | Holt |
| 7,696,241 B2 | 4/2010 | Li et al. |
| 7,795,204 B2 | 9/2010 | Gardiner et al. |
| 7,825,084 B2 | 11/2010 | Harris et al. |
| 8,217,077 B2 | 7/2012 | Baxter et al. |
| 8,609,725 B2 | 12/2013 | Baxter et al. |
| 2001/0008641 A1 | 7/2001 | Krotzer |
| 2002/0035965 A1 | 3/2002 | Uni et al. |
| 2003/0092609 A1 | 5/2003 | Larsen et al. |
| 2003/0165604 A1 | 9/2003 | Tsubaki et al. |
| 2003/0176514 A1 | 9/2003 | Fuhrmann et al. |
| 2003/0203070 A1 | 10/2003 | Lin et al. |
| 2004/0013787 A1 | 1/2004 | Theuer |
| 2004/0048925 A1 | 3/2004 | Wiley et al. |
| 2004/0071825 A1 | 4/2004 | Lockwood |
| 2004/0106678 A1 | 6/2004 | Dobbins et al. |
| 2004/0122210 A1 | 6/2004 | Thim et al. |
| 2004/0202770 A1 | 10/2004 | Cain et al. |
| 2004/0237466 A1 | 12/2004 | Grossmann et al. |
| 2004/0248771 A1 | 12/2004 | Raggi |
| 2005/0075280 A1 | 4/2005 | Larsen et al. |
| 2005/0106219 A1 | 5/2005 | Bortlik et al. |
| 2005/0215640 A1 | 9/2005 | Baxter et al. |
| 2005/0249650 A1 | 11/2005 | Damhuis et al. |
| 2006/0193961 A1 | 8/2006 | Shastri et al. |
| 2006/0204632 A1 | 9/2006 | Barrett-Reis et al. |
| 2006/0286210 A1 | 12/2006 | Rangavajla et al. |
| 2006/0293220 A1 | 12/2006 | Holt |
| 2007/0093553 A1 | 4/2007 | Baxter et al. |
| 2007/0125785 A1 | 6/2007 | Robinson et al. |
| 2007/0142469 A1 | 6/2007 | Thomas et al. |
| 2008/0031860 A1 | 2/2008 | Hageman |
| 2008/0058415 A1 | 3/2008 | Shulman et al. |
| 2008/0119552 A1 | 5/2008 | Navarro |
| 2008/0193624 A1 | 8/2008 | Shulman et al. |
| 2008/0194407 A1 | 8/2008 | Ashmead et al. |
| 2008/0254153 A1 | 10/2008 | Wang et al. |
| 2008/0260923 A1 | 10/2008 | Kratky et al. |
| 2008/0274230 A1 | 11/2008 | Johns et al. |
| 2008/0305531 A1 | 12/2008 | Lam et al. |
| 2008/0317886 A1 | 12/2008 | Sparkman |
| 2009/0087540 A1 | 4/2009 | Haschke et al. |
| 2009/0110674 A1 | 4/2009 | Loizou |
| 2009/0220637 A1 | 9/2009 | Roessle |
| 2009/0263367 A1 | 10/2009 | Foley |
| 2010/0179112 A1 | 7/2010 | Rathmacher et al. |
| 2011/0218244 A1 | 9/2011 | Kneller |
| 2011/0256301 A1 | 10/2011 | Kensler et al. |
| 2012/0141448 A1 | 6/2012 | De Ferra et al. |
| 2012/0177744 A1 | 7/2012 | Thomas |
| 2012/0177752 A1 | 7/2012 | Baxter |
| 2012/0178811 A1 | 7/2012 | Thomas |
| 2012/0189714 A1 | 7/2012 | Baxter |
| 2012/0189715 A1 | 7/2012 | Baxter |
| 2012/0189716 A1 | 7/2012 | Baxter |
| 2012/0189717 A1 | 7/2012 | Baxter |
| 2012/0196829 A1 | 8/2012 | Baxter |
| 2013/0011498 A1 | 1/2013 | Baxter |

FOREIGN PATENT DOCUMENTS

| | | |
|---|---|---|
| DE | 29707308 | 6/1997 |
| DE | 10145818 C1 | 10/2002 |
| EP | 0036663 | 9/1981 |
| EP | 0367724 A1 | 9/1990 |
| EP | 0385859 A1 | 9/1990 |
| EP | 698078 | 8/1997 |
| EP | 9739749 A2 | 10/1997 |
| EP | 0637239 B1 | 8/1999 |
| EP | 1968564 A2 | 9/2008 |
| EP | 2082738 A1 | 7/2009 |
| JP | 05503508 A | 6/1993 |
| JP | 7507569 T | 8/1995 |
| JP | 9121809 A | 5/1997 |
| JP | 11508282 T | 7/1999 |
| JP | 2001288107 A | 10/2001 |
| JP | 2002518440 A1 | 6/2002 |
| JP | 2002521428 A | 7/2002 |
| JP | 2003137790 A | 5/2003 |
| JP | 2009155336 | 7/2009 |
| JP | 5145033 | 11/2012 |
| WO | 9011073 | 10/1990 |
| WO | 9406417 A1 | 3/1994 |
| WO | 9414429 A1 | 7/1994 |
| WO | 9804253 A1 | 2/1998 |
| WO | 99/66917 A2 | 12/1999 |
| WO | 0006134 A2 | 2/2000 |
| WO | 01/77271 A2 | 10/2001 |
| WO | 03053456 | 7/2003 |
| WO | 03091214 | 11/2003 |
| WO | 2004064715 A2 | 8/2004 |
| WO | 2005000315 | 1/2005 |
| WO | 2005102301 A2 | 11/2005 |
| WO | 2006/062424 A2 | 6/2006 |
| WO | 2007066232 | 6/2007 |
| WO | 2007075605 A2 | 7/2007 |
| WO | 2009/143097 A1 | 11/2009 |
| WO | 2010068696 | 6/2010 |
| WO | 2011074995 | 6/2011 |
| WO | 2011156238 | 12/2011 |
| WO | 2012092035 | 7/2012 |
| WO | 2012097061 | 7/2012 |
| WO | 2013056048 | 4/2013 |
| WO | 2013170189 | 11/2013 |
| WO | 2013188258 | 12/2013 |

OTHER PUBLICATIONS

Office Action issued in U.S. Appl. No. 13/016,005, dated Jun. 1, 2012.

Examiner's First Report in Australian Patent Application No. 2006331950, dated Apr. 19, 2012.

Anonymous, "Reload Dietary Supplements," Database GNPD (Online) Mintel, May 2010, XP002676291, available at www.gnpd.com.

Charbonneau, "Recent case histories of food product-metal container interactions using scanning electron microscopy-x-ray microanalysis," Scanning, vol. 19(7), pp. 512-518 (1997).

International Search Report and Written Opinion for International Application No. PCT/US2012/024817, dated Jun. 6, 2012.

International Search Report and Written Opinion for International Application No. PCT/US2012/023767, dated Jun. 6, 2012.

Montanari et al., "Quality of Organic Coatings for Food Cans: Evaluation Techniques and Prospects of Improvement," Progress in Organic Coatings, vol. 29(1-4), pp. 159-165 (1996).

Final Office Action for U.S. Appl. No. 13/016,041, dated Jun. 8, 2012.

English translation of Office Action issued in Chinese Patent Application No. 201110084963, dated Mar. 30, 2012.

Office action issued in Chinese App. No. 200580009596.0, dated Jun. 28, 2010.

Office action issued in Taiwan App. No. 094109357, dated Dec. 2, 2010.

Oliver et al., "Airway Smooth Muscle and Asthma," Allergology International, vol. 55, pp. 215-223 (2006).

Ostaszewski et al., "3-Hydroxy-3-Methylbutyrate (HMB) Fed in the Water Enhance Immune Response in Young Broilers," Abstract 96, . 25.

Ostaszewski et al., "The immunomodulating activity of dietary 3-hydroxy-3-methylbutyrate (HMB) in weaning pigs," J. Anim. Sci., vol. 81, Supplemental 1, p. 136 (1998).

Ostaszewski et al., "The leucine metabolite 3-hydroxy-3-methylbutyrate (HMB) modifies protein turnover in muscles of laboratory rates and domestic chickens in vitro," J. Anim. Physiol. A. Anim. Nutr. 84, pp. 1-8 (2000).

Ostaszewski et al., "The effect of the leucine metabolite 3-hydroxy 3-methylbutyrate (HMB) on muscle protein synthesis and protein

(56) References Cited

OTHER PUBLICATIONS breakdown in chick and rat muscle," Journal of Animal Science, vol. 74, Supplemental 1, p. 138 (1996).
Ostaszewski et al., "Dietary supplementation of 3-hydroxy-3-methylbutyrate improved catch-up growth in underfed lambs," Ann. Zootech, vol. 43, p. 308 (1994).
Panton et al., "Effect of b-hydroxy-b-methylbutyrate and resistance training on strength and functional ability in the elderly," Medicine & Science in Sports & Exercise, p. S194 (1998).
Panton et al., "Nutritional supplementation of the leucine metabolite b-hydroxy-b-methylbutyrate (HMB) during resistance training," Nutrition, vol. 16, pp. 734-739 (2000).
Papet et al., "The effect of a high dose of 3-hydroxy-3-methylbutyrate on protein metabolism in growing lambs," Br. J. Nutr., vol. 77, pp. 885-896 (1997).
Perkins et al., "Good cop, bad cop: the different faces of NF-kB," Cell Death and Differentiation, vol. 13, pp. 759-772 (2006).
Peterson et al., "Enhancement of cellular and humoral immunity in young broilers by the dietary supplementation of b-hydroxy-b-methylbutyrate," Immunopharmacology and Immunotoxicity, vol. 21, No. 2, pp. 307-330 (1999).
Peterson et al., "In Vitro Exposure with B-Hydroxy-B-Methylbutyrate Enhances Chicken Macrophage Growth and Function," Vetrinary Immunology and Immunopathology, vol. 67, pp. 67-78 (1999).
Porter et al., "Sustained NFAT Signaling Promotes a Th1-like Pattern of Gene Expression in Primary Murine CD4+ T Cells," Journal of Immunology, vol. 168, pp. 4936-4945 (2002).
Rathbacher et al., "Safety of a nutritional mixture of b-hydroxy-b-methylbutyrate (HMB), glutamine and arginine in healthy young adults and patients with AIDS," JPEN 23(1): S10 (1999).
Rathmacher et al., "The effect of the leucine metabolite b-hydroxy-b-methylbutyrate on lean body mass and muscle strength during prolonged bedrest," FASEB J., p. A909.
Rathmacher et al., "Supplementation with a combination of beta-hydroxy-beta-methylbutyrate (HMB), arginine, and glutamine is safe and could improve hematological parameters," Journal of Parenteral and Enternal Nutrition, vol. 28, No. 2, p. 65-75 (2004).
Sandberg et al., "Effect of b-hydroxy-b-methylbutyrate on the physiological response to exercise and conditioning in horses," Journal of Animal Science, p. 198 (1997).
Sandberg et al., "The Effect of Intensive Training and b-hydroxy-b-methylbutyrate (HMB) on Muscle Glycogen concentration in the Horse," Journal of Animal Science, vol. 76, Supplemental 1, p. 175 (1998).
Siwicki et al., "Immunomodulating effect of 3-hydroxy-3-methylbutyrate (HMB) on the nonspecific cellular and humaoral defense mechanisms in rainbow trout (*Oncorhynchus nykiss*)," Journal of Animal Science, vol. 76, Supplemental 1, p. 137, (1998).
Siwicki et al., "In Vitro Effects of 3-Hydroxy-3-methylbutyrate (HMB) on measures of immune function and immunocompetence in fish," Journal of Animal Science, vol. 76, Supplemental 1, p. 136 (1998).
Siwicki et al., "Influence of 3-hydroxy-3-methylbutyrate on specific cellular immune response after in vitro and in vivo immunization with *Yersinia ruckeri* antifen," Journal of Animal Science, vol. 76, Supplemental 1, p. 136 (1998).
Smith et al., "Mechanisms of the attenuation of proteolysis-inducing factor stimulated protein degradation in muscle by beta-hydroxy-beta-methylbutyrate." Cancer Research, pp. 8731-8735 (2004).
Talleyrand et al., "Effect of feeding b-hydroxy-b-methylbutyrate on immune function in stressed calves," FASEB J, p. A951 (1994).
Talleyrand et al., "Uptake and output of the leucine metabolite b-hydroxy-b-methylbutyrate (HMB) across the legs of pigs," FASEB J., p. A71 (1993).
Tisdale et al., "Inhibition of Weight Loss by w-3 Fatty Acids in an Experimental Cachexia Model," Cancer Research, vol. 50, pp. 5002-5026 (1990).

Van Koevering et al., "Effect of b-hydroxy-b-methylbutyrate on the health and performance of shipping-stressed calves," The Oklahoma State Animal Science Research Report, pp. 312-316 (1993).
Van Koevering et al., "Oxidation of leucine and a-ketoisocaproate to b-hydroxy-b-methylbutyrate in vivo," American Journal of Physiology, pp. E27-E31 (1992).
Vukovich et al., "Body composition of 70-year-old adults responds to dietary beta-hydroxy beta-methylbutyrate similarly to that of young adults," Journal of Nutrition, vol. 131, No. 7, pp. 2049-2052 (2001).
Vukovich et al., "Effect of beta-hydroxy beta-methylbutyrate on the onset of blood lactate accumulation and VO2 peak in endurance-trained cyclists," J. Strength & Conditioning Res., vol. 15, No. 4, pp. 491-497 (2001).
Vukovich et al., "The effect of dietary b-hydroxy-b-methylbutyrate (HMB) on strength gains and body composition in older adults," FASEB J., p. A376 (1997).
Williams et al., "Effect of a specialized amino acid mixture on human collagen deposition," Annals of Surgery, vol. 236, No. 3, pp. 369-375 (2002).
Witte et al., "Nutritional abnormalities contributing to cachexia in chronic illness," International Journal of Cardiology, vol. 85, pp. 23-31 (2002).
Zachwieja et al., "Effect of the Leucine Metabolite b-hydroxy-b-methylbutyrate on muscle protein synthesis during prolonged bedrest," FASEB Abstracts, p. A1025 (1999).
Zhang et al., "Change in plasma b-hydroxy-b-methylbutyrate (HMB) by feeding leucine, a-ketiusicaoriate and isovaleric acid to pigs," FASEB J., p. A392 (1993).
Examination Report for Vietnam Application No. 1-2006-01765, issued Aug. 18, 2011.
Andela, et al., "NFkappaB: a pivotal transcription factor in prostate cancer metastasis to bone," Clinical Orthopaedics and Related Research, vol. 415S, pp. S75-S85 (2003).
Andrews, et al. "A rapid micropreparation technique for extraction of DNA-binding proteins from limiting numbers of mammalian cells," Nucleic Acids Res., vol. 19, No. 9, p. 2499 (1991).
Battaini, "Protein kinase C isoforms as therapeutic targets in nervous systemdisease states," Pharmacological Research, vol. 44, No. 5, pp. 353-361 (2001).
Bibby et al., "Characterization of a transplantable adenocarcinoma of the mouse colon producing cachexia in recipient animals," J. Natl. Cancer Inst., vol. 78, No. 3, pp. 539-546 (1987).
Carter, "Protein Kinase C as a drug target: Implications for drug or diet prevention and treatment of cancer," Current Drug Targets, vol. 12, No. 2, pp. 163-183 (2000).
Coffman et al.,"Syntheses by Free-radical Reactions. V. A New Synthesis of Carboxylic Acids", J. Am. Chem. Soc., vol. 80, pp. 2282-2887 (1958).
Delfino, "Hormonal Regulation of the NF-kappaB signaling pathway," Molecular and Cellular Endocrinology, vol. 157, Nos. 1-2, pp. 1-9 (1999).
Dentener et al., "Systemic anti-inflammatory mediators in COPD: increase in soluble interleukin 1 receptor II during treatment of exacerbations," Thorax, vol. 56, No. 9, pp. 721-726 (2001).
Examiner's 2nd Report issued in New Zealand Application No. 568611, dated Jun. 3, 2011.
Fenteany et al., "Lactacystin, proteasome function and cell fate," J. Biol. Chem., vol. 273, No. 15, pp. 8545-8548 (1998).
Frank, "Potential new medical therapies for diabetic retinopathy: protein kinase C inhibitors," American Journal of Opthamology, vol. 133, No. 5, pp. 693-698 (2002).
Goekijan, "Protein kinase C in the treatment of disease: Signal transduction pathways, inhibitors, and agents in development," Current Medical Chemistry, vol. 6, No. 9, pp. 877-903 (1999).
Gomes-Marcondes et al., "Development of an in-vitro model system to investigate the mechanism of muscle protein catabolism induced by proteolysis-inducing factor," British Journal of Cancer, vol. 86, No. 10, pp. 1628-1633 (2002).
Jagoe, "What do we really know about the ubiquitin-proteasome pathway in muscle atrophy?" Current Opinion in Clinical Nutrition and Metabolic Care, vol. 4, No. 3, pp. 183-190 (2001).

(56) References Cited

OTHER PUBLICATIONS

Meier, "Protein kinase C activation and its pharmacological inhibition in vascular disease," Vascular Medicine, vol. 5, No. 3, pp. 173-185 (2000).
Moscat, "NF-kappaB activation by protein kinase C isoforms and B-cell function," EMBO Reports, vol. 4, No. 1, pp. 31-36 (2003).
O'Brianne et al., "The tumor promoter receptor protein kinase C: A novel target for chemoprevention and therapy of human colon cancer," Prog. Clin. Bio. Res., vol. 391, pp. 117-120 (1995).
Orino et al., "ATP-dependent reversible association of proteasomes with mutliple protein components to form 26S complexes that degrade ubiquitinated proteins in human HL-60 cells," FEBS Letters, vol. 284, No. 2, pp. 206-210 (1991).
Ostaszewski et al., "3-hydroxy-3-methylbutyrate and 2-oxoisocaproate effect body composition and cholestreol concentration in rabbits." Journal of Animal Physiology and Animal Nutrition, vol. 79, pp. 135-145 (1998).
Schols, "Evidence for a relation between metabolic derangements and increased levels of inflammatory mediators in a subgroup of patients with chronic obstructive pulmonary disease," Thorax, vol. 51, No. 8, pp. 819-824 (1996).
Schols, "Pulmonary cachexia," International Journal of Cardiology, vol. 85, No. 1, pp. 101-110 (2002).
Smart et al, "Polyclonal and allergen-induced cytokine responses in adults . . . " Journal of Allergy and Clinical Immunology, vol. 110, pp. 45-46 (2002).
Smith et al., "Effect of a cancer cachectic factor on protein synthesis/degradation in murine C2C12 myoblasts: modulation by eicosapentaenoic acid," Cancer Research, vol. 59, No. 21, pp. 5507-5513 (1999).
Smith et al., "Signal transduction pathways involved in proteolysis-inducing factor induced proteasome expression in murine myotubes," British Journal of Cancer, vol. 89, No. 9, pp. 1783-1788 (2003).
Takabatake et al., "Circulating leptin in patients with chronic obstructive pulmonary disease," American Journal of Respiratory and Critical Care Medicine, vol. 159, pp. 1215-1219 (1999).
Teixeira et al., "The role of interferon-c on immune and allergic responses . . . , " Mem. Inst. Oswaldo Cruz, vol. 100, pp. 137-144 (2005).
Todorov et al., "Characterization of a cancer cachectic factor," Nature, vol. 379, No. 6567, pp. 739-742 (1996).
Todorov et al., "Induction of muscle protein degradation and weight loss by a tumor product," Cancer Research, vol. 56, No. 6, pp. 1256-1261 (1996).
Toker, "Signaling through protein kinase C," Frontiers in Bioscience, vol. 3, pp. 1134-1147 (1998).
Van Koevering et al., "Effects of b-hydroxy-b-methylbutyrate on performance and carcass quality of feedlot steers." Journal of Animal Science, vol. 72, pp. 1927-1935 (1994).
Waalkes, "A fluorometric method for the estimation of tyrosine in plasma and tissues," Journal of Laboratory and Clinical Medicine, vol. 50, No. 5, pp. 733-736 (1957).
Watchorn et al., "Proteolysis-inducing factor regulates hepatic gene expression via the transcriptionfactor NF-kappaB and STST3," FASEB Journal, vol. 15, No. 3, pp. 562-564 (2001).
Whitehouse et al., "Induction of protein catabolism in myotubes by 15(S)-hydroxyeicosatetraenoic acid through increased expression of the ubiquitin-proteasome pathway," British Journal of Cancer, vol. 89, No. 4, pp. 737-745 (2003).
Whitehouse et al., "Increased expression of the ubiquitin-proteosome pathway in murine myotubes by proteolysis-inducing factor (PIF) is associated with activation of the transcription factor NF-kappaB," British Journal of Cancer, vol. 89, No. 6, pp. 1116-1122 (2003).
Wolf et al., "The mitogen-activated protein kinase signaling cascade: from bench to bedside," IMAJ, vol. 4, No. 8, pp. 641-647 (2002).
Haumann, "Structured Lipids Allow Fat Tailoring," International News on Fats, Oils, and Related Materials, vol. 8(10), pp. 1004-1011 (1997).

Ho et al., "Antioxidants, NFkappaB activation and diabetogenesis," Proceedings of the Society for Experimental Biology and Medicine, vol. 222, No. 3, pp. 205-213 (1999).
Kutsuzawa et al., "Muscle energy metabolism and nutritional status in patients with chronic obstructive pulmonary disease," American Journal of Respiratory and Critical Care Medicine, vol. 152, No. 2, pp. 647-652 (1995).
Lorite et al., "Activation of a TP-ubiquita-dependent proteolysis in skeletal muscle in vivo and murine myoblasts in vitro by a proteolysis-inducing factor (PIF)," British Journal of Cancer, vol. 85, No. 2, pp. 297-302 (2001).
Merck Index No. 1862, 2003.
Merck Index No. 5198, 2003.
Merck Index No. 7355, 2003.
Merck Index No. 9908, 2003.
Merck Index No. 9975, 2003.
International Search Report and Written Opinion for PCT/US2011/039170, dated Aug. 3, 2011.
European Search Report for App. 10186645.7-1216, dated Feb. 14, 2011.
Golubitskii et al., "Stability of Ascorbic Acid in Aqueous and Aqueous-Organic Solutions for Quantitative Determination," J. Anal Chem., vol. 62, No. 8, pp. 742-747 (2007).
Puspitasari et al., "Calcium Fortification of Cottage Cheese with Hydrocolloid Control of Bitter Flavor Defects," J. Dairy Sci., vol. 74, pp. 1-7 (1991).
Toelstede et al., "Sensomics Mapping and Identification of the Key Bitter Metabolites in Gouda Cheese," J Agric Food Chem, vol. 56, pp. 2795-2804 (2008).
Toelstede et al., "Quantitative Studies and Taste Re-Engineering Experiments Toward the Decoding of the Nonvolatile Sensometabolome of Gouda Cheese," J Agric Food Chem, vol. 56, pp. 5299-5307 (2008).
Tordoff et al., "Vegetable Bitterness is Related to Calcium Content," Appitite, vol. 52, pp. 498-504 (2009).
Engel et al., "Evolution of the Composition of a Selected Bitter Camembert Cheese During Ripening: Release and Migration of Taste-Active Compounds," J. Agric Food Chem, vol. 49, pp. 2940-2947 (2001).
Engel et al., "Evolution of the Taste of a Bitter Camembert Cheese During Ripening: Characterization of a Matrix Effect," J. Agric Food Chem., vol. 49, pp. 2930-2939 (2001).
Gacs et al., "Significance of Ca-Soap Formation for Calcium Absorption in the Rat," Gut, vol. 18, pp. 64-68 (1977).
Case Study: Water Purification Plant Installed at New UK Power Station, Filtration & Separation (Dec. 2004).
Kreider et al., "Effect of Calcium Beta-Hydroxy-Beta-Methylbutyrate (HMB) Supplementation During Resistance-Training on Markers of Catabolism, Body Composition and Strength," International Journal of Sports Medicine, vol. 20, No. 8, pp. 503-509 (Nov. 1, 1999).
International Search Report and Written Opinion for PCT/US2011/022928 (May 23, 2011).
International Search Report and Written Opinion for PCT/US2011/022932 (May 23, 2011).
International Search Report and Written Opinion for PCT/US2011/022938 (May 23, 2011).
International Search Report and Written Opinion for PCT/US2011/022947 (May 23, 2011).
International Search Report and Written Opinion for PCT/US2011/022935 (May 23, 2011).
De Maat et al., "Inflammation, Thrombosis and Atherosclerosis: Results of the Glostrup Study," Journal of Thrombosis and Haemostasis, 2003, vol. 1, No. 5, p. 950-957.
Choi et al., "Hematein inhibits atherosclerosis by inhibition of reactive oxygen generation and NF-kappaB-dependent inflammatory mediators in hyperlipidemic mice," Journal of Cardiovascular Pharmacology, 2003, vol. 42, No. 2, p. 287-295.
May, Patricia Eubanks, "Reversal of cancer-related wasting using oral supplementation with a combination of beta-hydroxy-beta-beta-methylbutyrate, arginine, and glutamine," American Journal of Surgery, vol. 183, No. 4, 2002, p. 471-479.

(56) References Cited

OTHER PUBLICATIONS

Sult, "Th1/Th2 Balance: A Natural Therapeutic Approach to Th2 Polarization in Allergy," Applied Nutritional Science Reports, 2003, p. 1-8.
AIDS Alert, 1999, vol. 14, No. 4, p. 41-43.
Clark et al., "Nutritional treatment for acquired immunodeficiency virus-associated wasting using beta-hydroxy beta-methylbutyrate, glutamine, and arginine: a randomized, double-blind, placebo-controlled study," Journal of Parenteral and Enteral Nutrition, May 2000, vol. 24, No. 3, p. 133-139.
Ostaszewski et al., "3-hydroxy-3-methylbuyric acid (HMB) in immunological reactions generated by nutritional allergy in guinea pigs," Veterinary Medicine, vol. 51, No. 2, 1995 (translation).
European Search Report and Opinion for Application No. 10186645. 7-1216, dated Feb. 14, 2011.
Office Action from Indian Patent Application No. 1372/MUMNP/2008, dated Sep. 23, 2010.
Office Action issued in Taiwan Application No. 094109357, dated Jun. 24, 2011.
Office Action issued in Japanese Application No. 2007-504991, dated Jun. 21, 2011.
Office Action issued in Russian Application No. 2008129605, dated Jul. 5, 2011.
Examiner's First Report issued for New Zealand Patent Application No. 593182, dated Jun. 3, 2011.
Smith et al., "Attenuation of Proteasome-Induced Proteolysis in Skeletal Muscle by B-hydroxy-B-methylbutyrate in Cancer-Induced Muscle Loss," Cancer Research, 2005, vol. 65(1), p. 277-283.
Siu et al., "Id2 and p53 participate in apoptosis during unloading-induced muscle atrophy," Am. J. Physiol. Cell. Physiol., vol. 288, C1058-C1073 (2005).
Ferrando et al., "Prolonged bed rest decreases skeletal muscle and whole body protein synthesis," Am. J. Physiol. vol. 270, pp. E627-E633 (1996).
Kortebein et al., "Effect of 10 days of Bed Rest on Skeletal Muscle in Healthy Older Adults," JAMA, vol. 297, pp. 1772-1774 (2007).
Zarzhevsky et al., "Recovery of muscles of old rats after hindlimb immobilisation by external fixation is impaired compared with those of young rats," Exp. Gerontol., vol. 36, pp. 125-140 (2001).
Hanson et al., "Seven days of muscle re-loading and voluntary wheel running following hindlimb suspension in mice restores running performance, muscle morphology and metrics of fatigue but not muscle strength," Muscle Res. Cell Motil., vol. 31, pp. 141-153 (2010).
Ballard et al., "Effect of I-glutamine supplementation on impaired glucose regulation during intravenous lipid administration," Nutrition, vol. 12(5), pp. 349-354 (1996).
Elam et al., "Effects of arginine and ornithine on strength, lean body mass and urinary hydroxyproline in adult males," The Journal of Sports Medicine and Physical Fitness, vol. 29(1), pp. 52-56 (1989).
Fligger et al., "Arginine Supplementation Increases Weight Gain, Depresses Antibody Production, and Alters Circulating Leukocyte Profiles in Preruminant Calves Without Affecting Plasma Growth Hormone Concentrations," J. Anim. Sci., vol. 75, pp. 3019-3025 (1997).
Jarowski et al., "Utility of Fasting Essential Amino Acid Plasma Levels in Formulation of Nutritionally Adequate Diets III: Lowering of Rat Serum Cholesterol Levels by Lysine Supplementation," Journal of Pharmaceutical Sciences, vol. 64(4), pp. 690-691 (1975).
Office Action issued in Chinese Application No. 200580009596.0, dated Jun. 9, 2011.
Office Action issued in Japanese Application No. 2000-555603, dated Jan. 12, 2010.
Office Action issued in Japanese Application No. 2000-555603, dated Feb. 15, 2011.
Office Action issued in Japanese Application No. 2000-555603, dated Oct. 25, 2011.
Office Action issued in Philippines Application No. 12006501893, dated Oct. 11, 2011.
Campbell, et al., "Allergic humans are hyporesponsive to a CXCR3 ligand-mediated Th1 immunity-promoting loop," The FASEB Journal, vol. 18, pp. 329-331 (2004).
Hauber, et al., "Expression of interleukin-4, interleukin-9 and interleukin-13 in peripheral blood mononuclear cells of cystic fibrosis patients with and without allergy," EXCIL Journal, vol. 5, pp. 209-216 (2006).
Office Action issued in Canadian Patent Application No. 2,560,042, dated Nov. 14, 2011.
Office Action issued in Russian Application No. 2008129605, dated Aug. 12, 2011.
Office Action issued in U.S. Appl. No. 11/025,466, dated Feb. 10, 2012.
Office Action issued in U.S. Appl. No. 13/016,005, dated Jan. 27, 2012.
Office Action issued in U.S. Appl. No. 13/016,041, dated Feb. 3, 2012.
European Search Report for Application No. 11187274.3-1216, dated Feb. 15, 2012.
Kritchevsky, "An international symposium on cancer cachexia, cytokines, and EPA: Introduction," Nutrition, Elsevier Inc., U.S., vol. 12(1), p. S1 (1996).
Notice of Preliminary Rejection for Korean Application No. 10-2006-7022383, dated Feb. 13, 2012.
First Hearing Notice in Indian Application No. 1372/MUMNP/2008, dated Nov. 4, 2011.
Second Hearing Notice in Indian Application No. 1372/MUMNP/2008, dated Mar. 10, 2012.
Tisdale et al., "Inhibition of lipolysis and muscle protein degradation by epa in cancer cachexia," Nutrition, Elsevier Inc., U.S., vol. 12(1), pp. S31-S33 (1996).
Zuljdgeest-Van Leeuwen et al, "Inhibition of lipolysis by eicosapentaenoic acid in weight-losing cancer patients and healthy volunteers," Clinical Nutrition, Churchill Livingstone, London, G.B., vol. 17, p. 13 (1998).
Abbott, "HMB (Beta-hydroxy-beta-methylbutyrate): A Scientific Review," Apr. 2010, pp. 1-34, XP002670332, available at http://abbottnutrition.com/downloads/resourcecenter/hmb-a-scientific-review.pdf (last accessed Apr. 9, 2012).
"Lite Protein Drinks," Database GNPD (Online) Mintel, Mar. 2000, XP002670334, available at www.gnpd.com.
"Lite Protein Drink Mixes with GlycerLEAN," Database GNPD (Online) Mintel, Feb. 2002, XP002670335, available at www.gnpd.com.
"Lean DynamX," XP 002670342, available at http://www.fitpage.de/produicte/pd-1330122620.htm?categoryId=181 (last accessed Feb. 24, 2012) (5 pages total).
International Search Report and Written Opinion for International Application No. PCT/US2011/066096, dated Mar. 14, 2012.
Meletis et al., "Natural Supports for Gaining and Maintaining Muscle Mass," Alternative and Complementary Therapies, pp. 257-263 (2005).
Zhang et al., "Occurrence of beta-hydroxy-beta-methylbutyrate in foods and feeds," Faseb Journal, vol. 8(4-5), p. A464 (Abstract 2685) (1994).
English translation of Notice of Rejection in Japanese Application No. 2000-555603, dated Mar. 6, 2012.
Non-final Office Action for U.S. Appl. No. 13/016,059, dated Mar. 23, 2012.
English translation of Office Action for Taiwan Patent Application No. 095147808, dated Mar. 21, 2012.
Rham et al., "Role of Ionic Environment in Insolubilization of Whey Protein During Heat Treatment of Whey Products," Journal of Dairy Science, vol. 67(5), pp. 939-949 (1984).
Non-final Office Action for U.S. Appl. No. 13/151,911, dated Apr. 19, 2012.
Office Action issued in Philippines Patent Application No. 1-2008-501331, dated Apr. 4, 2012.
Office action issued in Chinese Patent Application No. 200580009596, dated Mar. 1, 2012.
Second Office Action issued in Japanese Patent Application No. 2007-504991, dated Mar. 13, 2012.

(56) References Cited

OTHER PUBLICATIONS

Examination Report issued in New Zealand Patent Application No. 599371, dated Apr. 20, 2012.
International Preliminary Report on Patentability for International Application No. PCT/US2011/022938, dated Jan. 25, 2012.
International Preliminary Report on Patentability for International Application No. PCT/US2011/022947, dated Feb. 15, 2012.
Aggarwal et al., "Suppression of the Nuclear Factor kB Activation Pathway by Spice-Derived Phytochemicals: Reasoning for Seasoning", Annals of the New York Academy of Science, vol. 1030, pp. 434-441 (2004).
Barber et al., "The effect of an oral nutritional supplement enriched with fish oil on weight-loss in patients with pancreatic cancer," British Journal of Cancer, 1999, pp. 80-86, vol. 81, No. 1.
Barnes et al., "NF-kappa B: a pivotal role in asthma and a new target for therapy", Trends in Pharmacological Sciences, 1997, pp. 46-50, vol. 18.
Beck et al., "Anticachectic and Antitumor Effect of Eicosapentaenoic Acid and Its Effect on Protein Turnover," Cancer Research, vol. 51, pp. 6089-6093 (1991).
Brennan et al., "Nitrogen Metabolism in Cancer Patients," Cancer Treatment Reports, vol. 65, Supplemental 5, pp. 67-78 (1981).
Evans et al., "Expression and activation of protein kinase C in eosinophils after allergen challenge," Am J Physiol Lung Cell Mole Physiol, vol. 277, pp. 233-239 (1999).
Examination Report for Malaysian App. PI20082097 dated Jul. 29, 2011.
Examination Report from NZ Patent Application No. 568611, dated Apr. 13, 2010.
Flakoll et al., "Effect of b-hydroxy-b-methylbutyrate, arginine and lysine supplementation on strength, functionality, body composition, and protein metabolism in elderly women," Nutrition, vol. 20, pp. 445-451 (2004).
Fuller et al., "Decreasing male broiler mortality by feeding the leucine catabolite b-hydroxy-b-methylbutyrate," Poult. Sci., vol. 73, Supplemental 1, p. 93 (1994).
Gallagher et al., "B-hydroxy-b-methylbutyrate ingestion, Part 1: Effects on strength and fat free mass," Med. Sci. Sports Exerc, vol. 32, No. 12, pp. 2109-2115 (2000).
Gallagher et al., "b-hydroxy-b-methylbutyrate ingestion, Part II: effects on hematology, hepatic and renal function," Med. Sci. Sports Exerc., vol. 32, No. 12, pp. 2116-2119 (2000).
HMB, www.interactivenutrition.com, last visited Dec. 29, 2004.
International Search Report and Written Opinion for PCT/US2005/007951, dated Aug. 24, 2006.
International Search Report and Written Opinion for PCT/US2006/048303, dated May 6, 2008.
Jowko et al., "Creatine and b-hydroxy-b-methylbutyrate (HMB) additively increase lean body mass and muscle strength during a weight-training program", Nutrition, vol. 17, pp. 558-566 (2001).
Juven product information, http://abbottnutrition.com/Products/Juven, 5 pages, dated 2010.
Kaizen Hmb, www.bodybuilding.com, last visited Dec. 29, 2004.
Kisner, "The Nutrition of the Cancer Patient," Cancer Treatment Reports, vol. 65, Supplemental 5, pp. 1-2 (1981).
Knitter et al., "Effects of b-hydroxy-b-methylbutyrate on muscle damage after a prolonged run," J. Appl. Physiol., vol. 89, pp. 1340-1344 (2000).
Lentsch et al., "Activation and Regulation of NFkB during Acute Inflammation," Clin. Chem. Lab. Med., vol. 37, No. 3, pp. 205-208 (1999).
Levenhagen et al., "Arginine, Lysine, and b-hydroxymethylbutyrate (HMB) Supplementation Enhances the Efficiency of Protein Synthesis in Elderly Females," Nutrition Week Abstracts, vol. 75, pp. 411S-412S (2002).
Macchi et al., "Influence of co-ingestion of glucose on b-hydroxy-b-methylbutyrate (HMB) metabolism in humans," FASEB J., p. A909 (1999).
Miller et al., "The effect of intensive training and b-hydroxy-b-methylbutyrate (HMB) on the physiological response to exercise in horses." FASEB J., p. A290 (1997).
Milne et al., "Do Routine Oral Protein and Energy Supplements Improve Survival and Reduce Length of Hospital Stay for Elderly People," Nutrition Week Abstracts, p. 412S (2002).
Moschini et al., "Effect of feeding b-hydroxy-b-methylbutyrate (HMB) on leucine and fat metabolism in mammary gland," FASEB J., p. A70 (1993).
Nissen et al., "b-hydroxy-b-methylbutyrate (HMB) supplementation in humans is safe and may decrease cardiovascular risk factors," J. Nutr., vol. 130, pp. 1937-1945 (2000).
Nissen et al., "Colostral milk fat percentage and pig performance are enhanced by feeding the leucine metabolite b-hydroxy-b-methylbutyrate to sows," J. Anim. Sci., vol. 72, pp. 2331-2337 (1994).
Nissen et al., "Effect of b-hydroxy-b-methylbutyrate (HMB) supplementation of strength and body composition of trained and untrained males undergoing intense resistance training," FASEB J., p. A287 (1996).
Nissen et al., "Effect of dietary supplements on lean mass and strength gains with resistance exercise: A meta analysis," J. Appl. Physiol., vol. 94, pp. 651-659 (2003).
Nissen et al., "Effect of feeding b-hydroxy-b-methylbutyrate (HMB) on body composition and strength of women," FASEB J., p. A150 (1997).
Nissen et al., "Effect of leucine metabolite b-hydroxy-b-methylbutyrate on muscle metabolism during resistance-exercise training," J. Appl. Physiol., vol. 81, No. 5, pp. 2095-2104 (1996).
Nissen et al., "Nutritional role of the leucine metabolite b-hydroxy-b-methylbutyrate (HMB)," J. Nutr. Biochem., vol. 8, pp. 300-311 (1997).
Nissen et al., "The effect of b-hydroxy-b-methylbutyrate on growth, mortality and cacass qualitiies of broiler chickens," Poultry Science, vol. 71, pp. 137-155 (1994).
Nissen et al., "The effects of the leucine catabolite, b-hydroxy-b-methylbutyrate (HMB), on the growth and health of growing lambs," J. Anim. Sci., p. 243 (1994).
Nonnecke et al., "Leucine and its Catabolites After Mitogen-Stimulated DNA Synthesis by Bovine Lymphocytes," J. Nutr., vol. 121, pp. 1665-1672 (1991).
Office Action for U.S. Appl. No. 11/025,466, dated Oct. 4, 2010.
Office Action for U.S. Appl. No. 11/025,466, dated Dec. 5, 2008.
Office Action for U.S. Appl. No. 11/025,466, dated Apr. 14, 2010.
Office Action for U.S. Appl. No. 11/025,466, dated Apr. 6, 2011.
Office Action for U.S. Appl. No. 11/025,466, dated May 5, 2008.
Office Action for U.S. Appl. No. 11/025,466, dated Jun. 25, 2009.
Office Action for U.S. Appl. No. 11/025,466, dated Aug. 17, 2007.
Office Action for U.S. Appl. No. 11/025,466, dated Sep. 8, 2011.
Office Action for U.S. Appl. No. 11/641,978, dated Oct. 20, 2009.
Office Action for U.S. Appl. No. 11/641,978, dated Feb. 26, 2008.
Office Action for U.S. Appl. No. 11/641,978, dated Mar. 3, 2009.
Office Action for U.S. Appl. No. 11/641,978, dated Jun. 7, 2010.
Office Action from Chinese Patent Application No. 200680047936.3, dated Feb. 24, 2011.
Office Action from Chinese Patent Application No. 200680047936.3, dated May 25, 2010.
English translation of relevant portions of Israeli Office Action for Application No. 178039 dated Aug. 6, 2012.
Office action in Japanese Application No. 2008-547409 dated Jun. 5, 2012.
Examiner's Decision of Rejection from Japanese Application No. 2008-547409 dated Sep. 25, 2012.
English translation of Notice of Final Rejection for Korean Application No. 10-2006-7022383 dated Nov. 7, 2012.
First Office action from Mexican Appl. No. PA/a/2006/010922 dated Aug. 31, 2011.
Second Office Action from Mexican Appl. No. PA/a/2006/010922 dated Apr. 17, 2012.
Further Office Action from Mexican Appl. No. PA/a/2006/010922 dated Oct. 24, 2012.
Office Action in Mexican Appl. No. MX/a/2010/012154 dated Apr. 30, 2012.

(56) References Cited

OTHER PUBLICATIONS

Office Action in Mexican Appl. No. MX/a/2010/012154 dated Oct. 5, 2012.
Examination Report issued in New Zealand Application No. 599371 dated Dec. 5, 2012.
English translation of Office action rejecting Taiwan patent application No. 095147808 dated Nov. 8, 2012.
Allergy Online Clinic "Clinical Aspect in Th1 and Th2 Balance," http://allergyclinic.wordpress.com/2012/04/01/clinical-aspect-in-th1-and-th2-balance/; posted on Apr. 1, 2012, accessed on Dec. 21, 2012, 14 pages.
Alon et al., "Supplementing with beta-hydroxy-beta-methylbuturate (HMB) to build and maintain muscle mass: a review", Research Communications in Molecular Pathology and Pharmacology (2002) vol. 111, No. 1-4, pp. 139-151.
Barnes et al., "The cytokine network in asthma and chronic obstructive pulmonary disease", Journal of Clinical Investigation, vol. 118, No. 11 Nov. 2008, pp. 3546-3556.
Barnes, "Pathophysiology of Allergic Inflammation," Immunological Reviews (2011), vol. 242, pp. 31-50.
Berger, "Science Commentary: Th1 and Th2 responses: what are they/" BMJ (Aug. 12, 2000), vol. 321, p. 424.
Biocompare "Th1 and Th2 Balance, Regulation and Involvement in Disease," http://www.biocompare.com/Application Notes/43518-Th1-And-Th2-Balance-Regulation-And-Involvement-In-Disease/ posted on Apr. 24, 2006, accessed on Feb. 5, 2013 8 pages.
Cousins, et al., "Therapeutic approaches for control of transcription factors in allergic disease," J Allergy Clin Immunol, (Apr. 2008), vol. 21, No. 4 pp. 803-809.
De Los Reyes, et al., "Overview of resistance training diet, hormone replacement and nutritional supplements on age-related sarcopenia—a mini review", Research Communications in Molecular Pathology and Pharmacology, vol. 113-114, pp. 159-170 (2003).
Elias, et al., "New insights into the pathogenesis of asthma", Journal of Clinical Investigation, vol. 111, No. 3 (Feb. 2003) pp. 291-297.
Fisher, et al. "Effects of Oxandrolone and L-Glutamine on Body Weight, Body Cell Mass, and Body Fat in Patients with HIV Infection—Preliminary Analysis." Nutrition (1997), vol. 13, No. 3, Abstract P-12, p. 279.
Hooper, "Overview of NFkB Signaling" http://www.abcam.com/index.html?Pageconfig+respirce&rid=112255&pid=10629; accessed on Dec. 21, 2012 4 pages.
Kaslow, "Immune Restoration," http://www.drkaslow.com/html/immune_restoration.html; accessed on Dec. 21, 2012 9 pages.
Lucey et al., "Type 1 and Type 2 Cytokine Dysregulation in Human Infectious, Neoplastic, and Inflammatory Diseases", Clinical Microbiology Reviews, Oct. 1996, pp. 532-562.
MacDonald et al., "Understanding and Managing Cancer Cachexia,", Journal of the American College of Surgeons, vol. 197(1), 2003, pp. 143-161.
Merck Manual, "Starving and Wasting," 16th Ed., pp. 919-920 (1995)—submitted in Japanese with English explanation.
Nevala, et al., "Evidence of Systemic Th2-Driven Chronic Inflammation in Patients with Metastatic Melanoma," Clin Can Res (2009) vol. 15, pp. 1931-1939.
Wang et al., "Effect of Curcumin on Airway Inflammation and the Expression of Nuclear Factor kappa-B in Rats with Asthma", Chinese Journal of Clinical Rehabilitation, vol. 9, No. 11, p. 104 Mar. 21, 2005; with English Explanation.
Wang et al., "Effect of Curcumin on Aiway Collagen Deposition and the Expression of Transformation Growth Factor beta-1 in Rats with Asthma", Journal of Clinical Pediatrics, vol. 23, No. 9, p. 659; with English Explanation, 2005.
Orange Juice Facts, downloaded from www.orangejuicefacts.com/nutrition.html downloaded on Nov. 28, 2012 pp. 1-3 of 3.
Restriction Office Action in U.S. Appl. No. 10/810,762 dated Nov. 24, 2006.
Response to Restriction Office Action in U.S. Appl. No. 10/810,762 dated Dec. 18, 2006.
Office Action in U.S. Appl. No. 10/810,762 dated Mar. 22, 2007.
Response under 37 CFR 1.111 for U.S. Appl. No. 10/810,762 dated Sep. 24, 2007.
Office Action in U.S. Appl. No. 10/810,762 dated Mar. 18, 2008.
Notice of Abandonment for U.S. Appl. No. 10/810,762 dated Sep. 29, 2008.
Examiner Initiated Interview Summary in U.S. Appl. No. 10/810,762 dated Sep. 29, 2008.
Office Action from U.S. Appl. No. 13/347,985 dated Feb. 14, 2013.
Office Action from U.S. Appl. No. 11/641,978 dated May 21, 2013.
Office Action from U.S. Appl. No. 13/347,774 dated Apr. 25, 2013.
Office Action from U.S. Appl. No. 13/348,024 dated Mar. 20, 2013.
Response to Office Action and Terminal Disclaimer for U.S. Appl. No. 13/348,026 dated May 23, 2013.
Office Action from U.S. Appl. No. 13/347,877 dated Apr. 5, 2013.
Office Action from U.S. Appl. No. 13/347,956 dated Apr. 18, 2013.
Office action from Canadian Application No. 2,807,787 dated Apr. 15, 2013.
Notification to Grant Patent for Chinese Application No. 200680047936.3 dated Mar. 4, 2013 with English translation.
English translation of Second Office action for Chinese Application No. 201110084963 dated Dec. 21, 2012.
English summary of Second Expert Report in EC Appl. No. SP-06-6873 dated Mar. 27, 2013.
Notice of Allowance from Japanese Application No. 2008-547409 dated Feb. 26, 2013, granting 13 claims (English Translation of Granted Claims attached).
Further Office Action in Mexican Appl. No. MX/a/2010/012154 dated Mar. 12, 2013.
Exam Report issued in Philippines Application No. 12006501893 dated Mar. 22, 2013.
Grammatikos, Alexander, "The genetic and environmental basis of atopic diseases", Annals of Medicine, 2008 (40) pp. 482-495.
Hawkley, et al., "Stress and the aging immune system," Brain, Behavior and Immunity 18 (2004), pp. 114-119.
Medical News Today, "All About Asthma", downloaded from http://www.medicalnewstoday.com/info/asthma/types-of-asthma.php on May 10, 2013 3 pages.
Final office action for U.S. Appl. No. 13/347,757 dated Jun. 10, 2013.
Restriction Requirement for U.S. Appl. No. 13/347,978 dated May 10, 2013.
First Office Action for Vietnam Application No. 1-2006-01765 dated Apr. 11, 2013, with English summary.
Office Action from U.S. Appl. No. 13/348,035 dated Jun. 6, 2013.
Restriction Requirement for U.S. Appl. No. 11/025,466 dated Apr. 9, 2007.
Response to Restriction Requirement for U.S. Appl. No. 11/025,466 dated Apr. 19, 2007.
Response to Office Action for U.S. Appl. No. 11/025,466 dated Jun. 17, 2011.
Response under CFR1.111 for U.S. Appl. No. 11/025,466 dated Jan. 17, 2008.
Response under CFR1.111 for U.S. Appl. No. 11/025,466 dated Sep. 5, 2008.
Response Under 37 CFR 1.111 for U.S. Appl. No. 11/025,466 dated Jun. 2, 2009.
Response under 37 CFR 1.111 for U.S. Appl. No. 11/025,466 dated Dec. 18, 2009.
Response after RCE for U.S. Appl. No. 11/025,466 dated Aug. 6, 2010.
Response to Office Action from U.S. Appl. No. 11/025,466 dated Feb. 3, 2011.
Amendment and Response After RCE for U.S. Appl. No. 11/025,466 dated Dec. 8, 2011.
Amendment and Response to Ex Parte Quayle Action in U.S. Appl. No. 11/025,466 dated Feb. 14, 2012.
Notice of Allowance for U.S. Appl. No. 11/025,466 dated Mar. 22, 2012.
Response to Restriction Requirement in U.S. Appl. No. 11/641,978 dated Jan. 15, 2008.
Response to office action for U.S. Appl. No. 11/641,978 dated Jun. 26, 2008.
Response to Office Action for U.S. Appl. No. 11/641,978 dated Nov. 5, 2008.

(56) References Cited

OTHER PUBLICATIONS

Amendment filed with RCE for U.S. Appl. No. 11/641,978 dated Aug. 31, 2009.
Office Action for U.S. Appl. No. 11/641,978 dated Oct. 20, 2009.
Response to Office Action for U.S. Appl. No. 11/641,978 dated Jan. 19, 2010.
Interview Summary for U.S. Appl. No. 11/641,978 dated Mar. 26, 2010.
Response after RCE for U.S. Appl. No. 11/641,978 dated Sep. 13, 2010.
Office action for U.S. Appl. No. 11/641,978 dated Sep. 14, 2012.
Response in U.S. Appl. No. 11/641,978 dated Feb. 14, 2013.
Office action in U.S. Appl. No. 13/347,757 dated Jul. 30, 2012.
Response to Restriction/Election Requirement from U.S. Appl. No. 13/347,757 dated Aug. 30, 2012.
Office Action from U.S. Appl. No. 13/347,757 dated Dec. 6, 2012.
Office Action from U.S. Appl. No. 13/347,774 dated Oct. 4, 2012.
Response to Office Action from U.S. Appl. No. 13/347,774 dated Feb. 4, 2013.
Office Action from U.S. Appl. No. 13/348,026 dated Jan. 23, 2013.
Notice of Allowance for Canadian Application No. 2,560,042 dated Sep. 24, 2012.
Office action from Canadian Application No. 2,632,262 dated Nov. 26, 2012.
English translation of relevant portion of Third Office Action from Chinese Application No. 200680047936.3 dated May 30, 2012.
English summary of First Expert Report in EC Appl. No. SP-06-6873 dated May 7, 2012.
Communication in EP Application No. 11187274.3 dated Aug. 6, 2012.
Office Action in EP Application No. 10186645.7-1216 dated Nov. 7, 2012.
Response to Office Action from U.S. Appl. No. 13/347,757 dated Feb. 28, 2013.
Portal et al., "Effect of HMB supplementation on body composition, fitness, hormonal profile and muscle damage indices," Journal of Pediatric Endocrinology & Metabolism (Jul. 7, 2010), vol. 23, No. 7, pp. 641-650.
Tanaka et al., "Effects of the novel Foxo1 inhibitor AS1708727 on plasma glucose and triglyceride levels in diabetic db/db mice," European Journal of Pharmacology (2010), vol. 645, pp. 185-191.
Kornasio et al., "beta-hydroxy-beta-methylbutyrate (HMB) stimulates myogenic cell proliferation, differentiation and survival via the MAPK/ERK and PI3K/Akt pathways," Biochimica et Biophysica Acta (2009), vol. 1793, No. 5, pp. 755-763.
Nawa et al., "A novel Akt/PKB-interacting protein promotes cell adhesion and inhibits familial amyotrophic lateral sclerosis-linked mutant SOD1-induced neuronal death via inhibition of PP2A-mediated dephosphorylation of Akt/PKB," Cellular Signalling (2008), vol. 20, pp. 493-505.
Burke, Robert. "Inhibition of mitogen-activated protein kinase and stimulation of Akt kinase signaling pathways: Two approaches with therapeutic potential in the treatment of neurodegenerative disease," Pharmacology and Therapeutics (2007), vol. 114, pp. 261-277.
Damjanac et al., "Dissociation of Akt/PKB and ribosomal S6 kinase signaling markers in a transgenic mouse model of Alzheimer's disease," Neurobiology of Disease (2008), vol. 29, pp. 354-367.
Zdychova et al., "Emerging role of Akt Kinase/Protein Kinase B signaling in pathophysiology of Diabetes and its complications," Physiological Research (2005), vol. 54, pp. 1-16.
Extended European Search Report for EP 12382138.1 dated Oct. 16, 2012 (13 pages).
Notice of Abandonment for U.S. Appl. No. 13/347,757 dated Dec. 17, 2013.
Response to Office Action in U.S. Appl. No. 13/348,024 dated Jan. 21, 2014.
RCE and Response to Office Action for U.S. Appl. No. 13/348,035 dated Jan. 21, 2014.
Response to Office Action in U.S. Appl. No. 13/347,877 dated Jan. 9, 2014.
Notice of Allowance in U.S. Appl. No. 13/347,956 dated Dec. 2, 2013.
Office Action in U.S. Appl. No. 13/990,726 dated Feb. 4, 2014.
Notice of Rejection/Office Action in Japanese Application No. 2012-139422 date Oct. 22, 2013.
Office Action (Paper No. 8) issued in Philippines Application No. 1-2008-501331 dated Nov. 20, 2013.
Baier et al., "Year-long Changes in Protein Metabolism in Elderly Men and Women Supplemented with a Nutrition Cocktail of beta-hydroxy-beta-methylbutyrate (HMB), L-Arignine, and L-Lysine," JPEN (2009), vol. 33, No. 1, pp. 71-82 (Absract Only).
Wilson et al., "Review—Effects of beta-hydroxy-beta-methylbutyrate (HMB) on exercise performance and body composition across varying levels of age, sex and training experience: A Review," Nutrition and Metabolism, 2008 5:1, Jan. 2008 (17 pages).
Hudson et al., "Review—Maintaining muscle mass during extended disuse: aestivating frogs as a model species," The Journal of Experimental Biology, 205, 2297-2303 (2002).
Tisdale, MJ, "The ubiquitin-proteosome pathway as a therapeutic target for muscle wasting," J. Support Oncol., 3(3), pp. 209-217 (2005).
Amendment for U.S. Appl. No. 11/641,978 dated Aug. 21, 2013.
Pimental et al., "β-hydroxy-β-methylbutyrate (HMB) supplementation stimulates skeletal muscle hypertrophy in rats via the mTOR pathway," Nutrition and Metabolism, 8:11 (2011).
Fujiwara et al., "The Anti-Allergic Effects of Lactic Acid Bacteria are Strain Dependent and Mediated by Effects on both Th1/Th2 Cytokine Expression and Balance," Int. Arch. Allergy Immunol., vol. 135, pp. 205-215 (2004).
Lee, et al., :"D-pinitol regulates Th1/Th2 balance via supression Th2 immune response in ovalbumin-induced asthma," FEBS Letters, vol. 581, pp. 57-64 (2007).
Payne et al., "Nutritional Therapy Improves Function and Complements Corticosteroid Intervention in mdx Mice," Muscle & Nerve, 33, pp. 66-77 (2006).
Polte et al., "CD 137-mediated immunotherapy for allergic asthma," J. Clin. Invest, vol. 116, pp. 1025-1036 (2006).
Notice of Allowance for U.S. Appl. No. 11/641,978 dated Dec. 16, 2013.
Office Action from Canadian Application No. 2,632,262 dated Nov. 29, 2013.
International Search Report and Written Opinion for PCT/US2011/066258 dated Feb. 10, 2012.
International Preliminary Report on Patentability for PCT/US2011/0066258 dated Jul. 2, 2013.
International Search Report and Written Opinion for PCT/US2013/040608 dated Jun. 19, 2013.
International Search Report and Written Opinion for PCT/US2013/044899 dated Aug. 1, 2013.
Response after final action in U.S. Appl. No. 13/347,757 dated Aug. 12, 2013.
Advisory Action for U.S. Appl. No. 13/347,757 dated Aug. 28, 2013.
Response after Final Action for U.S. Appl. No. 13/347,774 dated Jun. 25, 2013.
RCE for U.S. Appl. No. 13/347,774 dated Aug. 12, 2013.
Advisory Action for U.S. Appl. No. 13/347,774 dated Aug. 12, 2013.
Notice of Abandonment for U.S. Appl. No. 13/347,985 dated Sep. 12, 2013.
Response to Restriction Requirement for U.S. Appl. No. 13/347,978 dated Jun. 10, 2013.
Office Action for U.S. Appl. No. 13/347,978 dated Aug. 22, 2013.
Amendment for U.S. Appl. No. 13/348,024 dated Jul. 19, 2013.
Office Action in U.S. Appl. No. 13/348,024 dated Sep. 18, 2013.
Notice of Allowance for U.S. Appl. No. 13/348,026 dated Aug. 2, 2013.
Amendment for U.S. Appl. No. 13/348,035 dated Sep. 5, 2013.
Final Office Action for U.S. Appl. No. 13/348,035 dated Oct. 18, 2013.
Amendment for U.S. Appl. No. 13/347,877 dated Aug. 5, 2013.
Office Action for U.S. Appl. No. 13/347,877 dated Oct. 9, 2013.
Response to Office Action for U.S. Appl. No. 13/347,956 dated Jul. 17, 2013.

(56) References Cited

OTHER PUBLICATIONS

Final Office Action for U.S. Appl. No. 13/347,956 dated Sep. 17, 2013.
Response to Office Action for U.S. Appl. No. 13/347,956 dated Nov. 18, 2013.
Office action from Canadian Application No. 2,807,787 dated Aug. 22, 2013.
Reexamination Notice for Chinese Application No. 200580009596.0, dated Jul. 9, 2013.
Decision on Rejection of CN Application No. 201110084963 dated Jul. 11, 2013.
Invitation Pursuant to Art. 94(3) and Rule 71(1) EPC in EP Application No. 06845745.6 dated Jul. 30, 2013.
Invitation Pursuant to Art. 94(3) and Rule 71(1) EPC in EP Application No. 09156851.9 dated Jul. 30, 2013.
Rule 161/162 Communication in EP Application No. 11808092.8 dated Aug. 2, 2013.
Letter Reporting Further Office Action for Mexican Appl. No. PA/a/2006/010922 dated Jul. 30, 2013.
Subsequent exam report issued in Phillippines Application No. 12006501893 mailed Sep. 4, 2013.
Search Report and Written Opinion in Singapore Application No. 201009417-5 dated Sep. 3, 2013.
English translation of Office Action for TW patent application No. 095147808 dated Jul. 16, 2013.
Hao, Yanlei et al., "Effects of Beta-Hydroxy-Beta-Methylbutyrate on Markers of Muscle Hypertrophy and Apoptotic Signaling During Reloading in Aged Rats Following Disuse," Medicine & Science in Sports & Exercise, vol. 42, No. 5, Suppl. 1, May 2010, p. 2, XP009156085.
Hao, Yanlei et al., "Beta-Hydroxy-Beta-Methylbutyrate Reduces Myonuclear Reduces Myonuclear Apoptosis During Recovery From Hind Limb Suspension-Induced Muscle Fiber Atrophy in Aged Rats," American Journal of Physiology—Regulatory Integrative and Comparitive Physiology, vol. 301, No. 3, Sep. 2011, pp. R701-R715, XP009156087.
Jank et al., "Effect of 3-hydroxy-3-methylbutyrate (HMB) on muscle cathepsins and calpain activities during the post-dexamethasone recovery period in young rats," Polish Journal of Veterinary Sciences, vol. 3, No. 4, pp. 213-218 (2000).
Lynch G.S., "Therapies for Improving Muscle Function in Neuromuscular Disorders," Exercise and Sport Sciences Reviews, Journal Pub Affiliates, vol. 29, No. 4, Oct. 1, 2001, pp. 141-148, XP008063778.
Rieu, et al., "Glucocorticoid excess induces a prolonged leucine resistance on muscle protein synthesis in old rats," Exp. Gerontol., 39(9), pp. 1315-1321 (2004).
Scheller, Eric S., et al., "The Effects of B-Hydroxy B-Methylbutyrate on Apoptotic Signaling and Recovery Following Disuse in Aged Rat Extensor Digitorum Longus Muscle," Medicine & Science in Sports & Exercise, vol. 42, No. 5, Suppl. 1, May 2010, p. 827, XP009156140.
Shah, et al., "Glucocorticoids oppose translational control by leucine in skeletal muscle," Am. J. Physiol. Endocrinol. Metab., 279: E1185-E1190 (2000).
Soares, JMC et al., "The Effects of Beta-Hydroxy-Beta-Methylbutyrate (HMB) on Muscle Atrophy Induced by Immobilization," Medicine and Science in Sports and Exercise, vol. 33, No. 5 Supl., May 2001, p. S140, XP009156086.
International Search Report and Written Opinion for PCT/US2013/061014 dated Feb. 6, 2014.
Notice of Allowance including Examiner Initiated Interview Summary in U.S. Appl. No. 11/641,978 dated Mar. 17, 2014.
Notice of Allowance in U.S. Appl. No. 13/348,024 dated Apr. 4, 2014.
Notice of Allowance in U.S. Appl. No. 13/348,035 dated Mar. 31, 2014.
Notice of Allowance in U.S. Appl. No. 13/347,877 dated Mar. 17, 2014.
Notice of Allowance in U.S. Appl. No. 13/347,956 dated Apr. 4, 2014.
Second Reexamination Notice for Chinese Application No. 200580009596.0 dated Feb. 27, 2014.
Communication in EP Application No. 11187274.3 dated Mar. 13, 2014.
English translation of Office Action in Japanese Application No. 2012-139422 dated Feb. 25, 2014.
English translation of Office Action in Japanese Application No. 2013-10874 dated Mar. 18, 2014.
Office Action (Paper No. 10) in Philippines Application No. 1-2008-501331 mailed Feb. 26, 2014.
Second Office Action in Vietnam Application No. 1-2006-01765 dated Feb. 27, 2014.

* cited by examiner

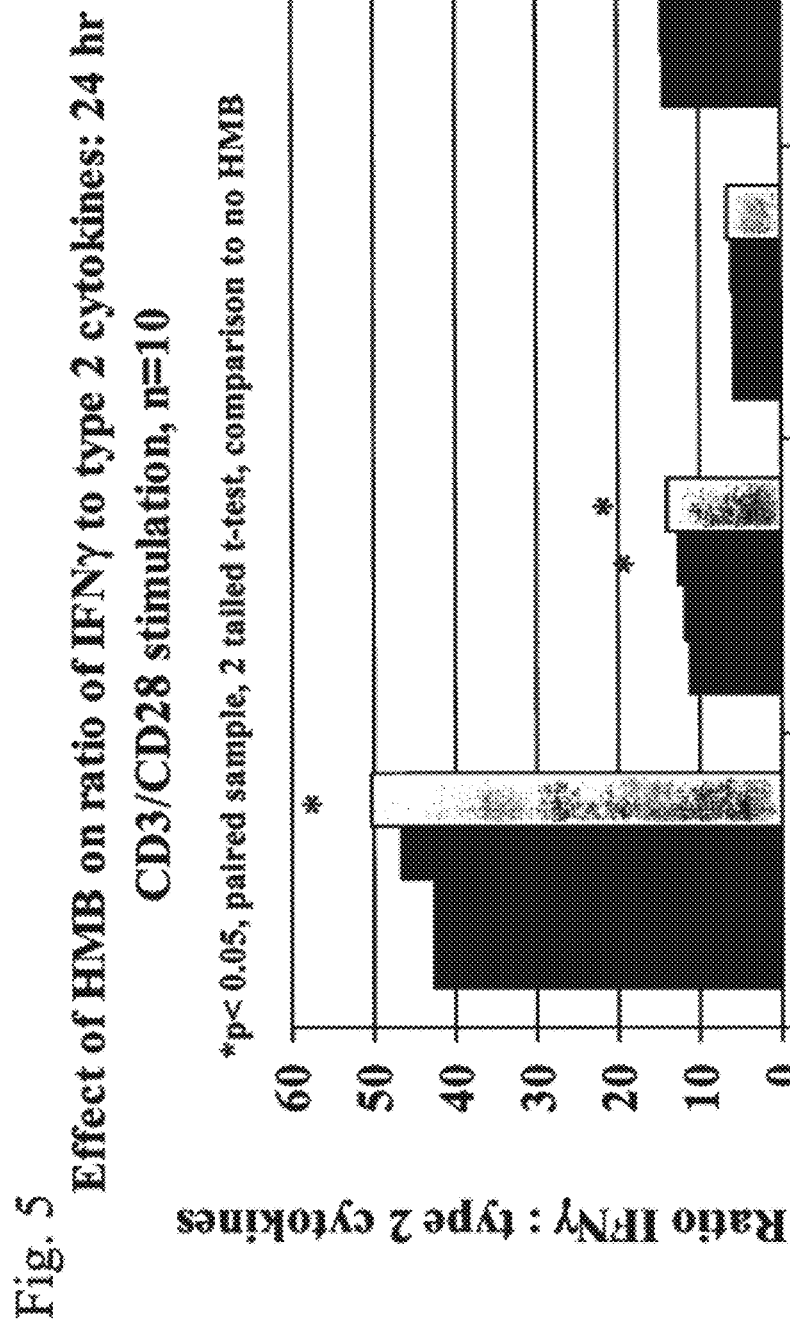
Fig. 5 Effect of HMB on ratio of IFNγ to type 2 cytokines: 24 hr CD3/CD28 stimulation, n=10

METHOD OF USING
β-HYDROXY-β-METHYLBUTYRATE TO
TREAT A CONDITION

This application is a divisional of U.S. application Ser. No. 11/641,978 filed Dec. 19, 2006, which claims the benefit of U.S. Provisional Patent Application 60/752,253 filed Dec. 19, 2005, the entire disclosures of which are incorporated herein by reference.

TECHNICAL FIELD

The present invention relates to a method of treating individuals with β-hydroxy-β-methylbutyrate (HMB) to modulate cytokine production.

BACKGROUND OF THE INVENTION

Allergies and asthma in the industrialized world have increased in prevalence and severity over recent years. Asthma is now, in fact, the most common chronic illness among children.

Much is known about the pathogenesis of allergies and asthma. Both are immune-based diseases. Both are associated with an imbalance in the relative levels of type-1 and type-2 cytokines in the body. It has been observed that individuals with allergies or asthma have a higher relative ratio of type 2 to type 1 cytokines. It is believed that this skewed ratio then contributes to the pathogenesis of allergies and asthma.

In general, cytokines are cell-produced regulatory proteins that influence, in paracrine or autocrine fashion, cell function. They are produced by immune cells and are therefore categorized by their inducible function and the cell types involved in the response.

Type 1 cytokines, for example, elicit or augment primarily cell-mediated immune responses against pathogens. Type 1 cytokines are involved in inflammatory responses, viral immunity, intracellular parasite immunity and allograft rejection. Type 1 cytokines include interleukin 2 (IL-2), interleukin 12 (IL-12), and interferon γ (IFNγ). Type 1 cytokines can suppress the production of type 2 cytokines.

Type 2 cytokines, by contrast, elicit or augment primarily antibody-mediated immune responses against pathogens. Type 2 cytokines are involved in humoral responses, helminth immunity, and allergic responses. Type 2 cytokines include interleukin 4 (IL-4), interleukin 5 (IL-5), interleukin 10 (IL-10), and interleukin 13 (IL-13). Type 2 cytokines can suppress the production of type 1 cytokines.

Given the association between cytokine imbalance in allergies and asthma, it is believed that therapies directed to the normalization of the ratio of type 1 to type 2 cytokine levels will help treat or even prevent such diseases. To that end, it has now been discovered herein that β-hydroxy-β-methylbutyrate (HMB) exposure (in vitro) increases the relative ratio of type-1 to type-2 cytokines in stimulated peripheral blood mononuclear cells (PBMC), thus providing a potential new therapy for treating individuals having or at risk for developing allergies and asthma.

As a commercially available ingredient, HMB is found in a variety of nutritional products. It is also a metabolite of the essential amino acid leucine and is therefore found naturally in the human body. HMB is also found in a variety of plants, including citrus fruits and alfalfa, as well as in catfish. It is also known and used for a variety of purposes, including to build or maintain muscle mass in appropriate individuals and to enhance overall immune function.

To date, however, there have been no reports on the effect of HMB in modulating type 1 and type 2 cytokine production nor any disclosure of the use of HMB to affect cytokine imbalance in treating conditions responsive thereto, including allergies and asthma.

SUMMARY OF THE INVENTION

The methods of the present invention are directed to the modulation of type 1 to type 2 cytokine levels in the body in those individuals afflicted with conditions characterized by a corresponding cytokine imbalance, to thus provide treatment of the underlying condition. Most notable among such conditions are allergies and asthma.

A first embodiment of the present invention is a method of treating an individual having a condition characterized by a relative imbalance of type 1 to type 2 cytokine levels in the body, wherein the method comprises the administration to the individual of an effective amount of β-hydroxy-β-methylbutyrate to thus modulate the imbalance, typically by increasing the relative levels or production of type 1 to type 2 cytokines. The present invention includes those embodiments in which the condition is asthma, allergies, or both.

A second embodiment of the present invention is a method of treating an individual having or at risk for developing allergies, the method comprising the administration to the individual an effective amount of β-hydroxy-β-methylbutyrate (HMB).

A third embodiment of the present invention is a method of treating individuals having or at risk for developing asthma, the method comprising the administration to the individual an effective amount of β-hydroxy-β-methylbutyrate (HMB).

A fourth embodiment of the present invention is a method of treating elderly individuals at risk for developing age-related infections, the method comprising the administration to such individuals an effective amount of β-hydroxy-β-methylbutyrate (HMB).

The present invention is based upon the discovery that peripheral blood mononuclear cells (PBMC) stimulated with the T cell stimulus CD3/CD28 and simultaneously exposed to HMB exhibit a shift in type 1 and type 2 cytokine production, favoring type 1 cytokine production. The shift occurs as HMB exposure increases the production of type 1 cytokines such as interferon-γ (IFNγ), interleukin 12 (IL-12), and interleukin 2 (IL-2), without a corresponding increase in the production of type 2 cytokines such as interleukin 4 (IL-4), interleukin 5 (IL-5), interleukin 10 (IL-10), and interleukin 13 (IL-13).

BRIEF DESCRIPTION OF THE DRAWINGS

FIG. 5 summarizes experimental data showing the effect of HMB on the ratio cytokine type 1 (IFNγ) to type 2 cytokines (IL-4, IL-5, IL-13, IL-10) from peripheral blood mononuclear cells simultaneously stimulated with CD3/CD28 for 24 hours (*p<0.05, paired sample, 2 tailed t-test, comparison to no HMB)

DETAILED DESCRIPTION

Figure 1:
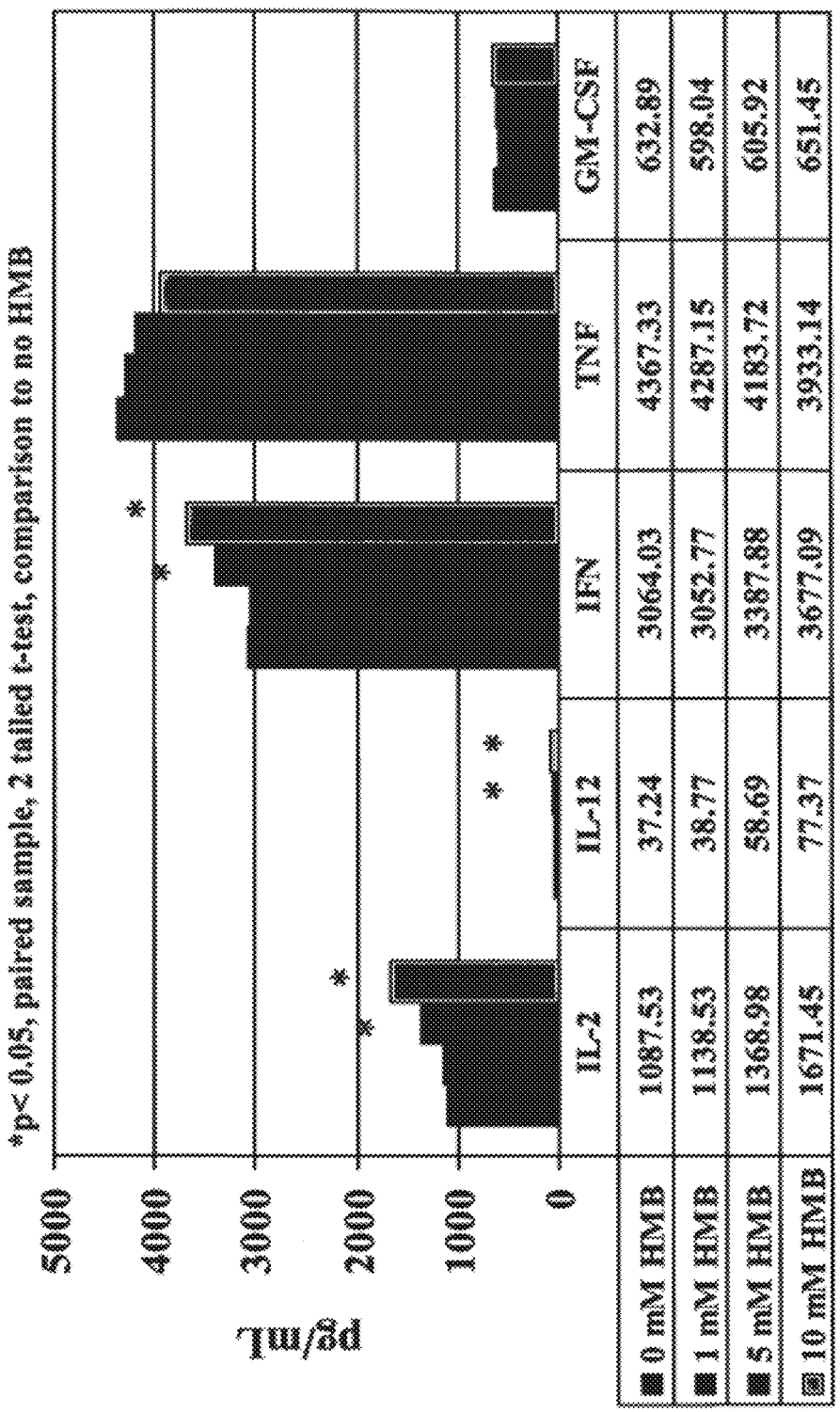
FIG. 1 summarizes experimental data showing the effect of HMB on type 1 cytokine (IL-2, IL-12, IFNγ, TNFα, GM-CSF) production from peripheral blood mononuclear cells simultaneously stimulated with CD3/CD28 for 24 hours ($*p<0.05$, paired sample, 2 tailed t-test, comparison to no HMB).

The methods of the present invention comprise the administration of an effective amount of β-hydroxy-β-methylbutyrate (HMB) to an individual in need thereof in the manner and for the purposes described herein. These and other essential or optional elements or features of the methods of the present invention are described in detail hereinafter.

The terms "treating" and "treatment" as used herein, unless otherwise specified, includes preventing a condition, delaying the onset of a condition, reducing the severity of symptoms of a condition, or eliminating some or all of the symptoms of a condition.

The term "ameliorate" as used herein, unless otherwise specified, means to eliminate, delay, or reduce the prevalence or severity of symptoms associated with a condition.

The term "condition" as used herein, unless otherwise specified, includes pathological and non-pathological conditions, all of which are characterized by an aberration or imbalance in the relative amounts of type 1 to type 2 cytokines.

The term "elderly individual" as used herein, unless otherwise specified, means someone more than 60 years old, preferably more than 70 years old.

The term "modulate" as used herein, unless otherwise specified, means to reduce the imbalance (i.e., imbalance associated with a condition) of type 1 to type 2 cytokine levels in the body, or to otherwise increase the ratio of type 1 to type 2 cytokines, including an increase in type 1 cytokine levels without a corresponding increase in type 2 cytokine levels.

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

All numerical ranges as used herein, whether or not expressly preceded by the term "about", are intended and understood to be preceded by that term, unless otherwise specified.

All references to singular characteristics or limitations of the present invention shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods of the present invention may also be substantially free of any optional or selected essential feature described herein, provided that the remaining method still contains all of the required limitations as described herein.

Embodiments

We now turn to the first embodiment of the present invention. Conditions included within the first embodiment of the present invention include allergy, asthma, solid tumors, cancers including advanced ovarian cancer and melanoma, kidney tumors, and stress, including psychological stress after a burn injury, surgical stress and pre-surgical stress. The methods are especially useful in treating allergy, asthma, or both.

With respect to allergy and asthma, elevated levels of IL-4, a type 2 cytokine, have been associated with the promotion or aggravation of allergy and asthma. Therefore, the first embodiment of the present invention, which is directed to a method of treating an individual having a condition comprising administering to the individual an amount of HMB effective to modulate or otherwise cause an increase in type 1 cytokine levels without a corresponding increase in type 2 cytokine levels, can treat individuals suffering from the symptoms of allergy and asthma because the increase in type 1 cytokines will serve to promote a balanced type 1 to type 2 cytokine profile.

With respect to cancers, including advanced ovarian cancer, studies have shown that the direct injection into the abdominal cavity of the type 1 cytokine IFN-γ may prolong the survival time for women with advanced ovarian cancer. This treatment has been shown to be effective both during the initial chemotherapy as well as after chemotherapy for individuals in whom chemotherapy has failed. Therefore, the first embodiment of the present invention, which is directed to a method of treating an individual having a condition comprising administering to the individual an amount of HMB effective to modulate or otherwise cause an increase in type 1 cytokine levels without a corresponding increase in type 2 cytokine levels, potentiates treatment of individuals with cancer, including advanced ovarian cancer, because the method has been discovered to raise levels of type 1 cytokines, including IFNγ.

With respect to kidney tumors and melanoma, studies have shown that interleukin 2 given as an injection under the skin can treat some kidney tumors and melanoma. When used as a cancer treatment, it is thought that IL-2 strengthens the body's natural defense mechanism and causes some cancer cells to be recognized and eliminated by immune cells. Therefore, the first embodiment of the present invention, which is directed to a method of treating an individual having a condition comprising administering to the individual an amount of HMB effective to modulate or otherwise cause an increase in type 1 cytokine levels without an increase in type 2 cytokines, potentiates treatment of individuals having kidney tumors or melanoma because the inventors have discovered that the method of the first embodiment of the present invention can raise levels of type 1 cytokines, including IL-2.

With respect to psychological stress after a burn injury, surgical stress and pre-surgical stress, studies have shown that stress increases type 2 and suppresses type 1 cytokine production. The immune system is compromised when individuals experience stress due to the production of type 2 cytokines and the suppression of type 1 cytokines that accompany periods of stress. Therefore, the first embodiment of the present invention, which is directed to a method of treating an individual having a condition comprising administering to the individual an amount of HMB effective to modulate or otherwise cause an increase in type 1 cytokine levels without an increase in type 2 cytokines, can treat stress after a burn injury, surgical stress and pre-surgical stress because administering to individuals an amount of HMB effective to increase type 1 cytokine levels without increasing type 2 cytokine levels accommodates for the cytokine imbalance associated with stress. The increase in type 1 cytokines promotes a balanced type 1 to type 2 cytokine profile in the individual.

The type 1 cytokines included within the first embodiment of the present invention include interferon-γ, interleukin 2, and interleukin 12. The type 2 cytokines included within the first embodiment of the present invention include interleukin 4, interleukin 5, interleukin 10, and interleukin 13.

Some of the protective functions of IFNγ include inhibition of viral replication, stimulation of macrophages and enhancement of cell surface molecules necessary for self-recognition in an immune response. Additionally, adequate levels of IFNγ are required for protection against infection and disease. IFNγ also antagonizes several actions of type 2 cytokine IL-4 and inhibits the proliferation of IL-4 producing cells. Therefore, the ability to induce production of IFNγ aids in the treatment of individuals with conditions such as those discussed herein. The inventors have discovered that HMB can induce the production of IFNγ without affecting the production of type 2 cytokines and therefore the present method is effective in treating conditions of the type discussed herein.

Some of the protective functions of IL-2 include inducing proliferation of all T cells, activated B cells, and natural killer cell and enhancing killing of tumor cells by the induction of tumoricidal cytokines from T cells and natural killer cells. Adequate levels of IL-2 are also required for protection against infection and disease. Therefore, the ability to induce production of IL-2 aids in the treatment of individuals with conditions such as those discussed herein. The inventors have discovered that administration of HMB induces the production of IL-2 without increasing the type 2 cytokine levels and therefore the present method is effective in treating conditions of the type discussed herein.

While adequate levels of type 2 cytokine IL-4 are also required for protection against infection and disease, elevated levels of IL-4 have been associated with the promotion of allergies, asthma and stress. Therefore, the ability to treat an individual having a condition as described herein is dependent upon both the ability to induce the production of type 1 cytokines such as IFNγ and IL-2, but also the ability to not simultaneously increase the production of type 2 cytokines, and particularly IL-4, as increased levels of IL-4 are known to promote allergies, asthma and stress. The first embodiment of the present invention is directed to a method of treating an individual having a condition wherein the administration of HMB induces the production of IL-2 and IFNγ without a corresponding increase in IL-4 levels.

Another aspect of the first embodiment of the present invention is directed to a method of treating an individual having a condition characterized by an imbalance in type 1 and type 2 cytokines, comprising administering to the individual an amount of HMB effective to modulate or otherwise cause an increase in type 1 cytokine levels without a corresponding increase in type 2 cytokine levels, wherein the amount of HMB administered is an amount effective to ameliorate allergic symptoms. Elevated levels of type 2 cytokine IL-4 are associated with the promotion of allergies. But type 1 cytokines such as IFNγ antagonize several actions of IL-4 and inhibit the proliferation of IL-4 producing cells. Therefore, the present method is capable of ameliorating the symptoms of allergies when the amount of HMB administered to an individual is an effective amount to promote a balanced type 1 to type 2 cytokine profile.

Similarly, the present invention is directed to a method of treating an individual having a condition characterized by an imbalance in type 1 and 2 cytokines, comprising administering to the individual an amount of HMB effective to modulate or otherwise cause an increase in type 1 cytokine levels without a corresponding increase in type 2 cytokine levels, wherein the amount of HMB administered is an amount effective to ameliorate asthmatic symptoms. Elevated levels of type 2 cytokine IL-4 are associated with the promotion of asthma. But type 1 cytokines such as IFNγ antagonize several actions of IL-4 and inhibits the proliferation of IL-4 producing cells. Therefore, the present method is capable of ameliorating the symptoms of asthma when the amount of HMB administered to an individual is an effective amount to promote a balanced type 1 to type 2 cytokine profile.

Still another aspect of the first embodiment of the present invention is directed to a method of treating an individual having a condition characterized by an imbalance in type 1 and type 2 cytokines, comprising administering to the individual an amount of HMB effective to modulate or otherwise cause an increase in type 1 cytokine levels without a corresponding increase in type 2 cytokine levels, wherein the amount of HMB administered is an amount effective to prevent a decrease in $FEV_1$, or the forced expiratory volume in 1 second. Individuals suffering from severe and persistent asthma display a low $FEV_1$ percentage value, while those who suffer from only mild and intermittent asthma display a higher percentage value. Thus, in administering an amount of HMB effective to induce the production of type 1 cytokines without inducing the production of type 2 cytokines in order to decrease the promotion of asthma associated with imbalanced type 1 to type 2 cytokine profiles, the present method is capable of preventing a decrease in $FEV_1$.

Individuals who experience only mild and intermittent symptoms of asthma display a $FEV_1$ value of greater than or equal to 80%. Therefore, another aspect of the first embodiment of the present invention is directed to a method of treating an individual having a condition where cytokine production is induced, comprising administering to the individual an amount of HMB effective to cause an increase in type 1 cytokine levels without a corresponding increase in type 2 cytokine levels, wherein the amount of HMB administered is an amount effective to maintain basal $FEV_1$ above 80%. In altering the imbalanced type 1 to type 2 cytokine profiles associated with asthma through the method of the first embodiment of the present invention, the method is capable of maintaining basal $FEV_1$ above 80%.

We now turn to the second embodiment of the present invention. The present invention includes a method of treating allergy in an individual having or at risk for developing allergy, the method comprising the administration to the individual an amount of β-hydroxy-β-methylbutyrate effective to prevent or ameliorate symptoms of allergies. Individuals who are at risk for allergy include those who are already suffering from allergies and those who are genetically or otherwise predisposed to having allergies.

The term "allergies" as used herein includes hay fever, food allergies, allergic conjunctivitis, atopic dermatitis, inhalant (air born allergens) allergy, and other common allergies. Such allergies are often associated with exposure to allergens such as animal danders, pollens, insect stings or bites, house dust, house dust mites, molds, some drugs, and foods, especially fish, eggs, milk and nuts.

We now turn to the third embodiment of the present invention. The present invention includes a method of treating asthma in an individual having or at risk for asthma, the method comprising the administration to the individual of an amount of β-hydroxy-β-methylbutyrate effective to prevent or ameliorate asthmatic symptoms. Individuals who are at risk for asthma include those who are already suffering from asthma and those who are genetically or otherwise predisposed to having asthma.

We now turn to the fourth embodiment of the present invention. The present invention includes a method of treating elderly individuals at risk of developing age-related infections, including both bacterial and viral infections, respiratory and non-respiratory, the method comprising the administration to such individuals of an amount of β-hydroxy-β-methylbutyrate effective to reduce the risk or prevalence of such infections.

An effective amount of HMB, for the purposes of the methods described herein, most typically ranges from 0.1 g to 10 g, including from 0.5 g to 5.0 g, and also including from 1.0 g to 3.5 g, of HMB per day. The total daily dose may be administered as a single, divided, or continuous (or semi-continuous) dose (e.g., enteral feeding), every day or on selected intermittent days.

The methods of the present invention are preferably directed to oral administration.

Product Forms

The methods of the present invention may be directed to any product form suitable for the safe administration of an effective amount of HMB to the targeted population or selected individual, all in accordance with the methods herein. Such products include pharmaceutical dosage forms (e.g., capsules, tablets, liquids, topicals, etc.) as well as nutritional products.

Nutritional products for use herein further comprise one or more (preferably all) of fat, protein, carbohydrate, minerals, and vitamins. Such products include solids, liquids, powders, and gels.

Non-limiting examples of solid nutritional product forms suitable for use herein include snack and meal replacement products, including those formulated as bars, sticks, cookies or breads or cakes or other baked goods, frozen liquids, candy, breakfast cereals, powders or granulated solids or other particulates, snack chips or bites, and so forth.

Non-limiting examples of liquid nutritional product forms suitable for use herein include snack and meal replacement products such as those formulated as juices or other acidified beverages, milk or soy-based beverages, shakes, coffees, teas, carbonated beverages, non-carbonated beverages, enteral feeding compositions, and so forth. These liquid compositions are most typically formulated as suspensions or emulsions, but can also be formulated in any other suitable form such as solutions, liquid gels, and so forth.

Many different sources and types of proteins, lipids, and carbohydrates are known and can be used in the various nutritional products described herein, provided that the selected nutrients are safe and effective for oral administration and are compatible with the essential and other added ingredients.

Carbohydrates suitable for use in the nutritional products may be simple, complex, or variations or combinations thereof. Non-limiting examples of suitable carbohydrates include hydrolyzed or modified starch or cornstarch, maltodextrin, glucose polymers, sucrose, corn syrup, corn syrup solids, rice-derived carbohydrate, glucose, fructose, lactose, high fructose corn syrup, indigestible oligosaccharides (e.g., fructooligosaccharides), honey, sugar alcohols (e.g., maltitol, erythritol, sorbitol), and combinations thereof.

Carbohydrates suitable for use herein also include soluble dietary fiber, non-limiting examples of which include gum arabic, sodium carboxymethyl cellulose, guar gum, citrus pectin, low and high methoxy pectin, oat and barley glucans, carrageenan, psyllium and combinations thereof. Soluble dietary fiber is also suitable as a carbohydrate source herein, non-limiting examples of which include oat hull fiber, pea hull fiber, soy hull fiber, soy cotyledon fiber, sugar beet fiber, cellulose, corn bran, and combinations thereof.

Proteins suitable for use in the nutritional products include hydrolyzed, partially hydrolyzed or non-hydrolyzed proteins or protein sources, and can be derived from any known or otherwise suitable source such as milk (e.g., casein, whey), animal (e.g., meat, fish), cereal (e.g., rice, corn), vegetable (e.g., soy), or combinations thereof. The proteins for use herein can also include, or be entirely or partially replaced by, free amino acids known for use in nutritional products, non-limiting examples of which include tryptophan, glutamine, tyrosine, methionine, cysteine, arginine, and combinations thereof.

Fats suitable for use in the nutritional products include coconut oil, fractionated coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, and combinations thereof.

The concentration or amount of carbohydrate, protein, and carbohydrate in the nutritional compositions of the present invention can vary considerably depending upon the particular product form and the various other formulations and targeted dietary needs. These macronutrients are most typically formulated within any of the caloric ranges (embodiments A, B, or C) described in the following table.

|  | Nutritional Embodiments | | |
| --- | --- | --- | --- |
| Nutrients | A | B | C |
| Carbohydrate - % total calories | 1-98 | 10-75 | 30-50 |
| Fat - % total calories | 1-98 | 20-85 | 35-55 |
| Protein - % total calories | 1-98 | 5-70 | 15-35 |

The nutritional compositions for use herein may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, anti-oxidants, emulsifying agents, buffers, additional pharmaceutical actives, additional nutrients as described herein, sweeteners including artificial sweeteners (e.g., saccharine, aspartame, acesulfame K, sucralose) colorants, flavors, thickening agents and stabilizers, emulsifying agents, lubricants, and so forth.

The nutritional compositions for use herein may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The nutritional compositions for use herein may further comprise any of a variety of other additional minerals, non-limiting examples of which include calcium, phosphorus, magnesium, iron, zinc, manganese, copper, sodium, potassium, molybdenum, chromium, chloride, and combinations thereof.

Experiment

The following experiment is conducted to determine the relationship between HMB exposure and cytokine production.

To induce production of cytokines, PBMCs, isolated from peripheral blood of 10 normal healthy donors, are stimulated for 24 hours with the T cell stimulant CD3/CD28. Cytokine production is analyzed using a Bio-plex Cytokine Assay. The Bio-Plex technology is based on antibody-antigen interactions, wherein fluorescently labeled beads conjugated with antibody directed against the cytokine of interest bind target cytokine to the bead. This bead-cytokine complex is then exposed to a biotinylated detection antibody and a streptavidin-PE (phycoerythrin) reporter molecule. The signal from the reporter molecule is directly proportional to the amount of cytokine present, thus enabling cytokine quantification.

Each of the T cell-derived cytokines quantified in the experiment is described in the following table:

| Type 1 cytokines | |
|---|---|
| Interleukin 2 (IL-2) | Growth factor for all subpopulations of T cells and also promotes the proliferation of activated B cells |
| Interleukin 12 (IL-12) | Induces the synthesis of IFNγ, IL-2, and Tumor necrosis factor α (TNFα) from helper T cells committed to the production of type 1 cytokines (Th1 cells), promotes the generation of lymphokine activated killer cells, inhibits the synthesis of IgE production |
| Interferon γ (IFNγ) | Influences cell mediated mechanisms of cytotoxicity, has antiviral and antiparasitic activities and inhibits the proliferation of transformed cells |
| Granulocyte Macrophage colony stimulating factor (GM-CSF) | Stimulates the proliferation and differentiation of neutrophilic, eosinophilic, and monocytic lineages and activates the mature forms of these cell types |
| Tumor necrosis factor α (TNFα) | Induces cytolysis and cytostasis of tumor cells, enhances the proliferation of T cells, promotes the proliferation and differentiation of B cells in the presence of IL-2 |
| Type 2 cytokines | |
| Interleukin 4 (IL-4) | Promotes the proliferation and differentiation of activated B cells |
| Interleukin 5 (IL-5) | Promotes growth and differentiation of eosinophils |
| Interleukin 13 (IL-13) | Down-modulates macrophage activity, reduces pro-inflammatory cytokine production, induces human monocyte differentiation and B cell differentiation and proliferation |
| Interleukin 10 (IL-10) | Suppressive cytokine which down-regulates type 1 cytokine production |

A t-test (paired sample, two-tailed) is performed in which a broad range of type 1 and type 2 cytokines are evaluated from cultures with HMB compared to cultures and without HMB.

Significant dose response increases are then observed in the production of the following type 1 cytokines: IL-2 (5 mM and 10 mM HMB), IL-12 (5 mM and 10 mM HMB), and IFNγ, (5 mM and 10 mM HMB); the results of which are summarized in FIG. 1.

Figure 2:
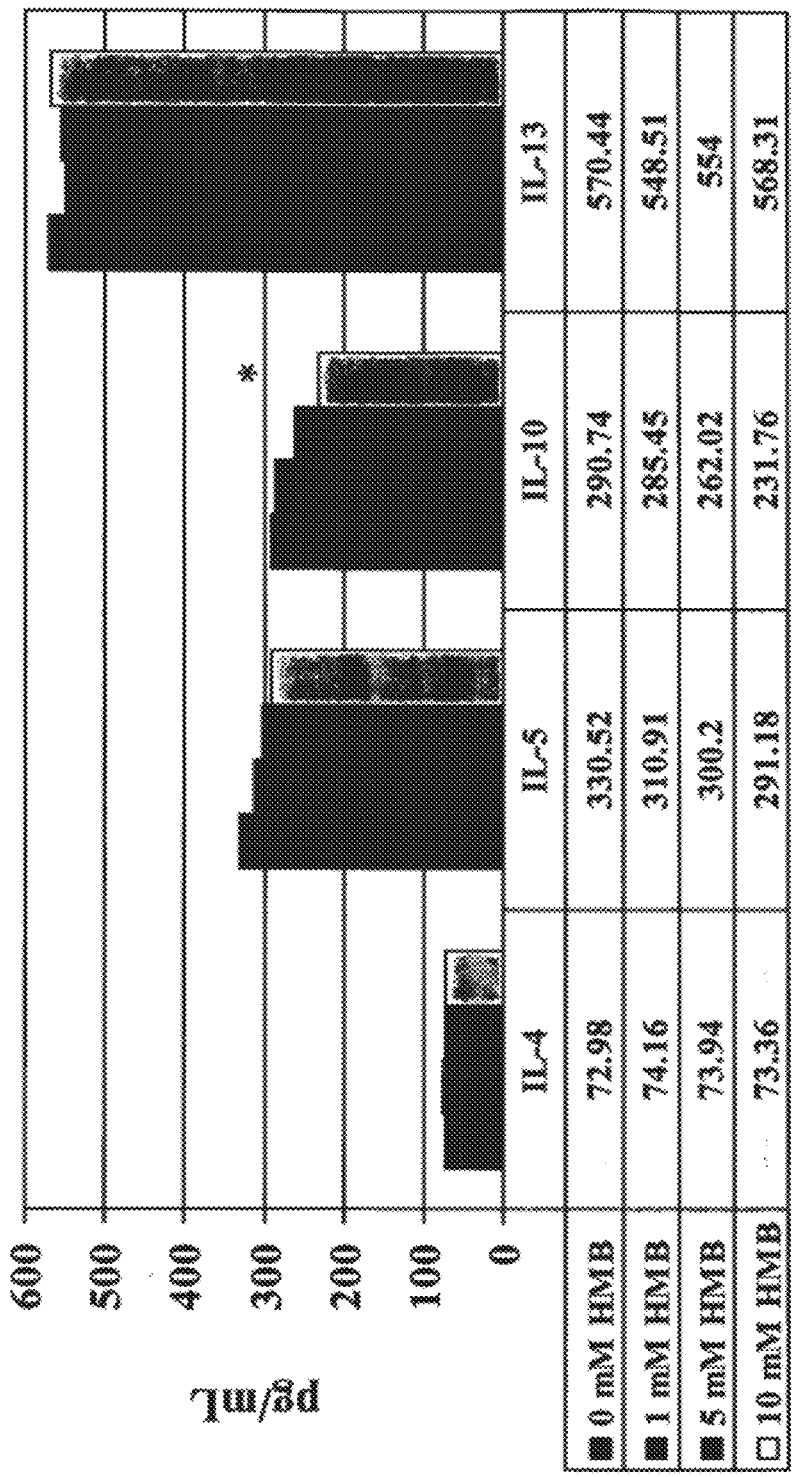
FIG. 2 summarizes experimental data showing the effect of HMB on type 2 cytokine (IL-4, IL-5, IL-10, IL-13) production from peripheral blood mononuclear cells simultaneously stimulated with CD3/CD28 for 24 hours ($*p<0.05$, paired sample, 2 tailed t-test, comparison to no HMB).

Concerning type 2 cytokine production, a significant decrease is seen in IL-10 production following 10 mM exposure to HMB (see FIG. 2), while HMB does not significantly affect the production of GC-CSF, TNFα, IL-4, IL-5, and IL-13. These results are summarized in FIG. 1 and FIG. 2.

Figure 3:
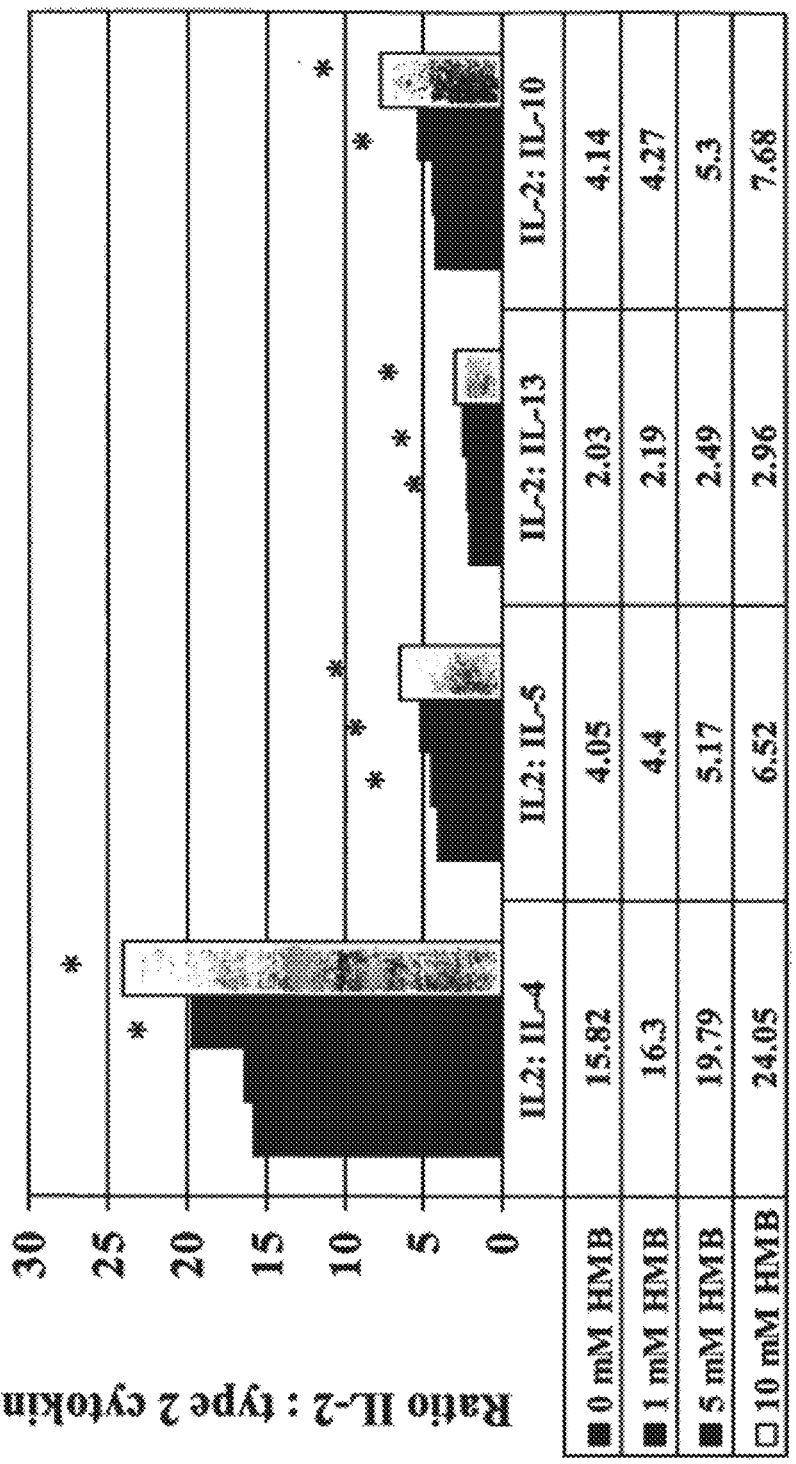
FIG. 3 summarizes experimental data showing the effect of HMB on the ratio cytokine type 1 (IL-2) to type 2 cytokines (IL-4, IL-5, IL-13, IL-10) from peripheral blood mononuclear cells simultaneously stimulated with CD3/CD28 for 24 hours ($*p<0.05$, paired sample, 2 tailed t-test, comparison to no HMB)
Figure 4:
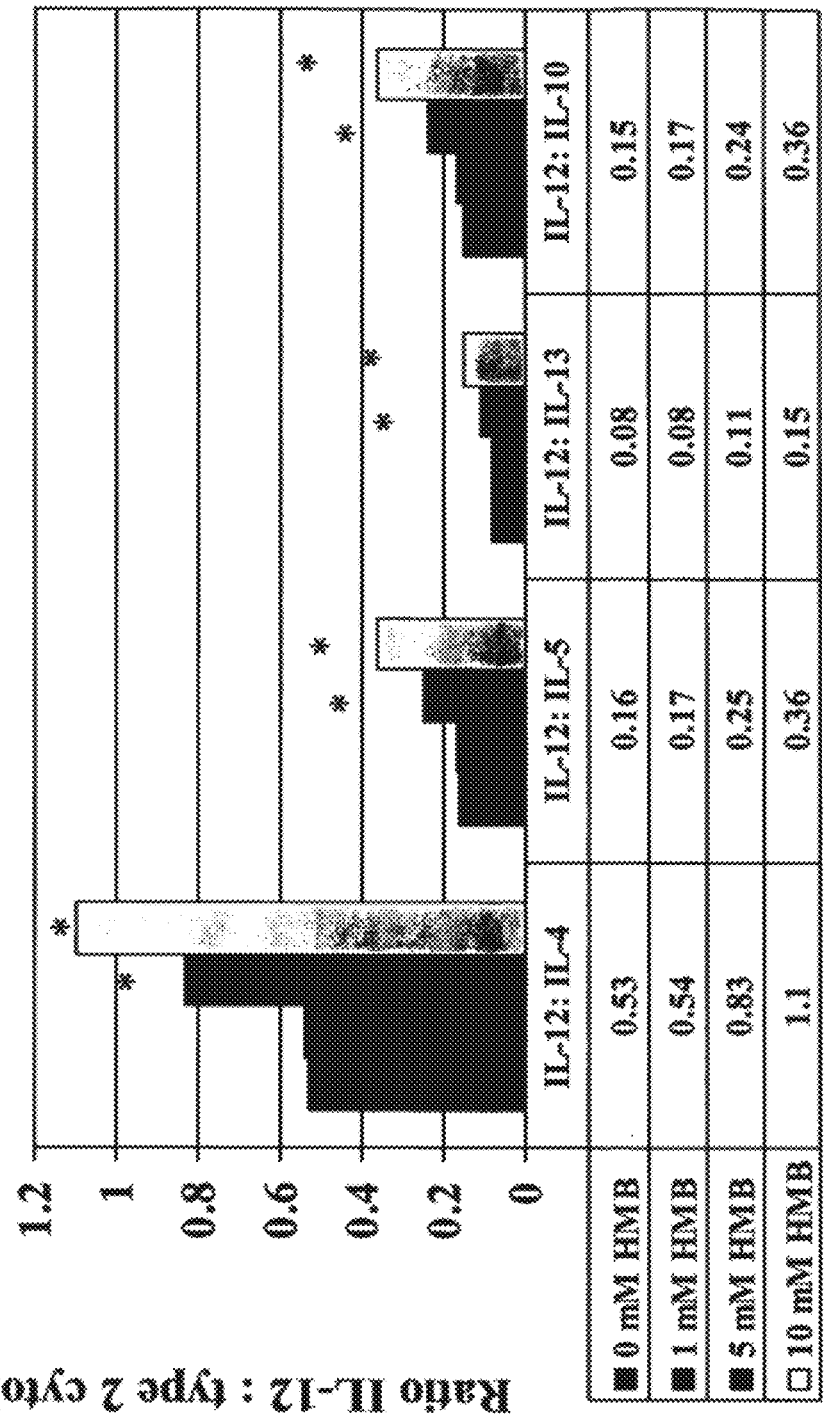
FIG. 4 summarizes experimental data showing the effect of HMB on the ratio cytokine type 1 (IL-12) to type 2 cytokines (IL-4, IL-5, IL-13, IL-10) from peripheral blood mononuclear cells simultaneously stimulated with CD3/CD28 for 24 hours (*p<0.05, paired sample, 2 tailed t-test, comparison to no HMB)

The shifts in cytokine production favoring type 1 are summarized in FIGS. 3, 4, and 5. Increases in IL-2 production relative to IL-4 and IL-10 production are demonstrated at HMB concentrations of 5 mM and 10 mM, while increased in IL-2 production relative to IL-5 and IL-13 production are demonstrated at HMB concentrations of 1 mM, 5 mM, and 10 mM (FIG. 3). Increases in IL-12 production relative to IL-4, IL-5, IL-13, and IL-10 are demonstrated at HMB concentrations of 5 mM and 10 mM (FIG. 4). Increases in IFNγ production relative to IL-4 and IL-10 are demonstrated at an HMB concentration of 10 mM, while relative to IL-5 increases are demonstrated at HMB concentrations of 5 mM and 10 mM (FIG. 5)

The data show that HMB exposure increases type 1 cytokine production (IL-2, IL-12, IFNγ) while reducing production of certain type 2 cytokines (IL-10) and not significantly affecting the production of other type 2 cytokines (GC-CSF, TNFα, IL-4, IL-5, IL-13). The net result, therefore, is a shift in type 1 and type 2 cytokine production in favor of type 1 cytokine production.

EXAMPLES

The following examples illustrate specific embodiments of the methods of the present invention, including some nutritional and other product forms suitable for use therein. The examples are given solely for the purpose of illustration and are not to be construed as limitations of the present invention, as many variations thereof are possible without departing from the spirit and scope of the invention.

The nutritional compositions described below are representative examples of nutritional products suitable for use in the methods of the present invention. Each may be prepared by conventional methods of making nutritional emulsion, some examples of which are described in U.S. Patent Publication 20050215640A1, which description is incorporated herein by reference.

| Liquid Nutritional #1 (Weight Gain Formula) | | | |
|---|---|---|---|
| Ingredient | Amt (kg) | Ingredient | Amt (kg) |
| Water | 316 | Vitamin DEK premix | 0.04 |
| Ultratrace/trace min. premix | 0.06 | Carrageenan | 0.03 |
| Potassium chloride | 0.072 | Soy lecithin | 0.6 |
| Na citrate | 2.89 | Sodium caseinate | 15.5 |
| Potassium iodide | 0.0001 | Calcium caseinate | 4.2 |
| Potassium citrate | 1.5 | Ca HMB monohydrate | 2.6 |
| Corn syrup | 7.68 | | |
| Maltodextrin | 53.6 | Milk protein isolate | 14 |
| Mg phosphate dibasic | 0.26 | Sardine oil | 6.9 |
| Ca phosphate tribasic | 0.99 | Ascorbic acid | 0.12 |
| Magnesium chloride | 1.2 | KOH 45% Soln | 0.13 |
| Sucrose | 11.9 | Taurine | 0.12 |
| Fructooligosaccharide | 5.9 | Water sol. vit. premix | 0.11 |
| Medium chain triglycerides | 2.6 | Ascorbyl palmitate | 0.03 |
| | | Choline chloride | 0.25 |
| Canola oil | 1.5 | L-carnitine | 0.0681 |
| Soy oil | 0.87 | Flavor #1 | 1.6 |
| 57% Vitamin A palmitate | 0.007 | Flavor #2 | 0.27 |

| Liquid Nutritional #2 (Low Glycemic Index Formula) | | | |
|---|---|---|---|
| Ingredient | Amt per 1,000 kg | Ingredient | Amt per 1,000 kg |
| Water | QS | Vitamin C | 584 gm |
| Maltodextrin | 56 kg | Potassium chloride | 530 gm |
| Acid casein | 41.09 kg | Choline chloride | 472.1 gm |
| Fructose | 28 kg | 45% KOH soln. | 402.5 gm |

Liquid Nutritional #2 (Low Glycemic Index Formula)

| Ingredient | Amt per 1,000 kg | Ingredient | Amt per 1,000 kg |
|---|---|---|---|
| High oleic safflower oil | 27.2 kg | UTM/TM premix | 369.3 gm |
| | | K phosphate | 333 gm |
| Maltitol syrup | 16 kg | Carnitine | 230.5 gm |
| Maltitol | 12.63 kg | Gellan gum | 125 gm |
| Fibersol 2E | 8.421 kg | Taurine | 100.1 gm |
| Caseinate | 6.043 kg | Vitamin E | 99 gm |
| FOS | 4.607 kg | Lutein Esters (5%) | 92 gm |
| Soy polysaccharide | 4.3 kg | WSV premix | 75.4 gm |
| | | Vit. DEK premix | 65.34 gm |
| Canola oil | 3.2 kg | 30% Beta carotene | 8.9 gm |
| Tricalcium phosphate | 2.8 kg | Vitamin A | 8.04 gm |
| | | Pyridoxine HCl | 3.7 gm |
| Mg chloride | 2.4 kg | Chromium chloride | 1.22 gm |
| Lecithin | 1.6 kg | Folic acid | 0.64 gm |
| Sodium citrate | 1.18 kg | Potassium iodide | 0.20 gm |
| Potassium citrate | 1.146 kg | Cyanocobalamin | 0.013 gm |
| Sodium hydroxide | 1.134 kg | Vitamin C | 584 gm |
| Mg phosphate | 1.028 kg | | |
| Calcium HMB monohydrate | 5.7 kg | | |
| m-inositol | 914 gm | | |

Liquid Nutritional #3 (Pediatric Formula)

| Ingredient | per 771 kg |
|---|---|
| Stock PIF Slurry | |
| High oleic safflower oil | 40.7 kg |
| Soy oil | 24.4 kg |
| MCT oil | 16.3 kg |
| Lecithin | 840.2 g |
| Monoglycerides | 840.2 g |
| Carrageenan | 508.9 g |
| Caseinate | 32.8 kg |
| Stock OSV Blend | |
| DEK premix | 83.3 g |
| Vitamin A | 7.1 g |
| Lutein esters (5%) | 92 g |
| Stock PIW Slurry | |
| Water | 530 kg |
| Caseinate | 11.3 kg |
| Whey protein | 11.9 kg |
| Stock MIN Slurry | |
| Water | 18 kg |
| Cellulose gum | 1696 g |
| Calcium HMB monohydrate | 4.4 kg |
| Magnesium chloride | 2.7 kg |
| Potassium chloride | 1.0 kg |
| Potassium citrate | 2.7 kg |
| Potassium iodide | 0.25 g |
| Dipotassium phosphate | 1.45 kg |
| Final Blend | |
| PIW slurry | 251 kg |
| PIF slurry | 53 kg |
| MIN slurry | 12.6 kg |
| Sodium chloride | 127.4 g |
| Sucrose | 77.6 kg |
| Tricalcium phosphate | 2.5 kg |
| Water | 167 kg |
| Stock WSF Soln | |
| Water | 31.7 kg |
| Potassium citrate | 3.74 g |
| UTM/TM premix | 172.2 g |
| WSV premix | 134.1 g |
| m-inositol | 176.7 g |

Liquid Nutritional #3 (Pediatric Formula)

| Ingredient | per 771 kg |
|---|---|
| Taurine | 145.5 g |
| L-carnitine | 34.92 g |
| Choline chloride | 638.7 g |
| Stock ascorbic acid soln. | |
| Water | 18.6 kg |
| Ascorbic acid | 550.0 g |
| 45% KOH | 341 g |
| Stock vanilla soln. | |
| Water | 38.5 kg |
| Vanilla flavor | 4.3 kg |

Nutritional Liquid #4 (Nutritional Supplement)

| Ingredient | per 1,000 kg | Ingredient | per 1,000 kg |
|---|---|---|---|
| Water | QS | Magnesium chloride | 558 gm |
| Corn Syrup | 33 kg | Vanilla Flavor | 544 gm |
| Maltodextrin | 28 kg | Sodium Chloride | 272 gm |
| Sucrose | 19.4 kg | Carrageenan | 227 gm |
| Caseinate | 8.7 kg | Choline chloride | 218 gm |
| Calcium HMB monohydrate | 5.7 kg | UTM/TM Premix | 165 gm |
| High Oleic Safflower Oil | 4.1 kg | Potassium Chloride | 146 gm |
| | | Ascorbic Acid | 145 gm |
| Canola Oil | 4.1 kg | Sodium Citrate | 119 gm |
| Soy Protein | 3.7 kg | Potassium Hydroxide | 104 gm |
| Whey Protein | 3.2 kg | | |
| Caseinate | 2.9 kg | Lutein (5%) | 46 gm |
| Corn Oil | 2.0 kg | WSV Premix | 33 gm |
| Tricalcium Phosphate | 1.4 kg | Vit DEK Premix | 29 gm |
| Potassium Citrate | 1.3 kg | Vitamin A | 3.7 gm |
| Magnesium Phosphate | 952 gm | Potassium Iodide | 86 mcg |
| Lecithin | 658 gm | | |

Liquid Nutritional #5 (Asthma and Allergy formula)

| Ingredient | kg per 1000 kg | Ingredient | kg per 1000 kg |
|---|---|---|---|
| Ingredient water | Q.S. | Natural Vitamin E | 0.645 |
| Borage oil | 61.1 | Micronized tri calcium phosphate | 0.631 |
| Marine oil | 53.4 | | |
| Milk protein isolate | 30.4 | Tocopherol-2 antioxidant | 0.600 |
| Sucrose | 11.7 | | |
| Whey protein conc. | 8.41 | Taurine | 0.456 |
| Gum arabic | 8.00 | Vanilla | 0.400 |
| Calcium HMB Monohydrate | 5.7 | Sucralose 25% sol | 0.375 |
| | | Zinc Sulfate | 0.251 |
| Soy lecithin | 4.77 | Ascorbyl palmitate | 0.143 |
| Cellulose gum | 4.00 | Sodium chloride | 0.143 |
| Potassium citrate | 2.64 | Acesulfame K | 0.0750 |
| Orange Cream Flavor | 2.50 | Cupric sulfate | 0.0177 |
| Ascorbic acid | 1.13 | FD&C Red #3 | 0.0150 |
| Turmeric powder | 1.00 | B carotene 30% | 0.00992 |
| Sodium citrate | 0.901 | Vit. A palmitate | 0.00315 |
| KOH 45% solution | 0.799 | Sodium molybdate | 0.000529 |
| Orange Oil | 0.750 | Sodium selenate | 0.000441 |

| Powder Nutritional #6 (Exercise Formula) | | | |
|---|---|---|---|
| Ingredient Name | Amount per 1000 kg | Ingredient Name | Amount per 1000 kg |
| Whey Protein Concentrate | 282.051 kg | Potassium Chloride | 5.128 kg |
| Calcium Caseinate | 192.308 kg | Salt | 3.205 kg |
| Maltodextrin | 165.416 kg | Xanthan Gum | 3.205 kg |
| Milk Protein Isolate | 138.782 kg | Choline Bitartrate 41% choline | 2.782 kg |
| Dutch Cocoa 10/12 | 76.932 kg | Acesulfame K | 2.718 kg |
| Sunflower Oil Creamer | 21.474 kg | Vanilla Disodium Phosphate | 1.923 kg |
| Myoplex Oil PreBlend | 19.231 kg | Anhydrous MicroChill WPI | 1.667 kg 1.282 kg |
| Chocolate Cream | 15.256 kg | Beta Carotene | 1.128 kg |
| Calcium HMB monohydrate | 13.157 kg | 1% CWS Sucralose | 692.3 g |
| Oat Fiber | 10.897 kg | Potassium Citrate | 641.0 g |
| Tricalcium Phosphate | 8.526 kg | 38% K Alpha Ketoglutaric Acid | 321.0 g |
| Vitamin Mineral Preblend | 8.462 kg | Egg Albumin Powder | 321.0 g |
| Dipotassium Phosphate | 8.333 kg | L-Glutamine | 321.0 g |
| Rich Dark Chocolate | 7.051 kg | Taurine | 321.0 g |
| Carrageenan CSM 2 | 6.474 kg | | |

Working Example I

A 28-year old individual who suffers from seasonal allergies in the spring is given 0.25-1 g of HMB (Nutritional Liquid #5) four times a week for a year. The symptoms of seasonal allergies are reduced the following spring.

Working Example II

A 30-year old white male who normally has four exacerbations of asthma per year is administered 1-10 g of HMB (Nutritional Liquid #5) four times a week for a year. Exacerbation frequency decreases to once a year.

Working Example III

A 45-year old female who has undergone chemotherapy for ovarian cancer is administered 2-10 g of HMB (Nutritional Liquid #1) four times a week for a year. One year later the ovarian cancer has not returned.

Working Example IV

A 50-year old male diagnosed with and has been treated for kidney tumors is administered 750 mg of HMB (capsules) four times a week for a year. Six months later the tumor has not spread to other parts of the individual's body.

Working Example V

A 42-year old female diagnosed with and treated for melanoma is administered 1 g of HMB 4 times ((Nutritional Liquid #1) a week for a year. Six months later the melanoma has not spread to other parts of the individual's body.

Working Example VI

A 37-year old male suffering from severe symptoms of psychological stress as a result of a burn injury is administered 500 mg (Nutritional Liquid #1) of HMB 4 times a week for a year. One year later the symptoms of psychological stress are reduced.

Working Example VII

A 29-year old female suffering from symptoms of surgical stress is administered 200 mg of HMB (Nutritional Liquid #2) 7 times a week for 2 months. Two months later the symptoms of surgical stress are reduced.

Working Example VIII

A 25-year old male suffering from symptoms of pre-surgical stress is administered 200 mg of HMB (capsules) once a day for 3 weeks preceding the individual's scheduled surgery. At the end of the 3 weeks, symptoms of pre-surgical stress are reduced.

Working Example IX

A 24-year old male suffering from moderate persistent asthma is tested to determine the individual's $FEV_1$ percentage value and the value is recorded. The individual is then administered 5-10 g of HMB 4 times ((Nutritional Liquid #5) a week for a year. One year later the individual's $FEV_1$ has not decreased and symptoms of asthma are reduced.

Working Example X

A 33-year old male suffering from mild intermittent asthma is tested to determine the individual's $FEV_1$ percentage value and a value of 83% is recorded. The individual is then administered 1.5-6 g of HMB 4 times (Nutritional Liquid #5) a week for a year. One year later the individual's $FEV_1$ remains above 80% and symptoms of asthma are reduced.

Working Example XI

A 14-year old female with a family history of seasonal allergies shows no signs of suffering from seasonal allergies. The individual is administered 0.1-1.5 g of HMB (Nutritional Liquid #3) once a day for 6 months. Six months later the individual still shows no signs of suffering from seasonal allergies.

Working Example XII

A 16-year old male with a family history of asthma shows no signs of suffering from the symptoms of asthma. The individual is administered 250 mg of HMB (Nutritional Liquid #4) once a day for 6 months. Six months later the individual still shows no signs of suffering from symptoms of asthma.

Working Example XIII

A 72 year old male, after conventional treatment for and recovery from pneumonia, is administered 250 mg of HMB (Nutritional Liquid #1) once a day for 6 months. During those six months, the individual remains free of respiratory tract infections, including any recurrence of pneumonia.

Working Example XIV

A 24-year old male is training for the New York Marathon. During his training period and for 3 months following the event he takes two servings per day of Nutritional formula #6 (containing 1 gram HMB per serving). Contrary to his previous year's experience, he does not experience any respiratory infections during this intense training regimen (such infections reflect the immune suppression that is known to be associated with extreme physical training programs).

What is claimed is:

1. A method of treating an individual having a condition characterized by a higher relative ratio of type 2 cytokines to type 1 cytokines, the method comprising administering to the individual a composition comprising an effective amount of β-hydroxy-β-methylbutyrate to increase the relative ratio of type 1 to type 2 cytokines, wherein said treating consists of at least one of delaying the onset of said condition and reducing the severity of symptoms of said condition, and wherein said condition is selected from the group consisting of allergy and asthma.

2. The method of claim 1 wherein the level of type 1 cytokines is increased by the administration of β-hydroxy-β-methylbutyrate without an increase in type 2 cytokines.

3. The method of claim 1 wherein the effective amount of β-hydroxy-β-methylbutyrate ranges from 0.1 grams to 10 grams per day.

4. The method of claim 3 wherein the effective amount of β-hydroxy-β-methylbutyrate ranges from 0.5 grams to 10 grams per day.

5. The method of claim 4 wherein the effective amount of β-hydroxy-β-methylbutyrate ranges from 0.5 grams to 5.0 grams per day.

6. The method of claim 5 wherein the effective amount of β-hydroxy-β-methylbutyrate ranges from 1.0 grams to 3.5 grams per day.

7. The method of claim 1 wherein the composition further comprises one or more of fat, protein, and carbohydrate.

8. The method of claim 1 wherein the condition is an allergy.

9. The method of claim 8 wherein the amount of β-hydroxy-β-methylbutyrate is effective to ameliorate symptoms of said allergy.

10. The method of claim 8 wherein the allergy is selected from the group consisting of hay fever, food allergies, allergic conjunctivitis, atopic dermatitis, and inhalant allergies.

11. The method of claim 1 wherein the condition is asthma.

12. The method of claim 11 wherein the amount of β-hydroxy-β-methylbutyrate is effective to ameliorate symptoms of said asthma.

13. The method of claim 11 wherein the amount of β-hydroxy-β-methylbutyrate is effective to prevent a decrease in forced expiratory volume in 1 second ($FEV_1$).

14. The method of claim 11 wherein the amount of β-hydroxy-β-methylbutyrate is sufficient to maintain basal forced expiratory volume in 1 second ($FEV_1$) above 80%.

15. The method of claim 1 wherein the type 1 cytokine is selected from the group consisting of interferon-γ, interleukin 2, and interleukin 12.

16. The method of claim 15 wherein the type 1 cytokine is interferon-γ or interleukin 2.

17. The method of claim 1 wherein the type 2 cytokine is selected from the group consisting of interleukin 4, interleukin 5, interleukin 13, and interleukin 10.

18. The method of claim 17 wherein the type 2 cytokine is interleukin 4.

19. The method of claim 1 wherein the composition further comprises a mineral selected from the group consisting of calcium, phosphorus, magnesium, iron, zinc, manganese, copper, sodium, potassium, molybdenum, chromium, chloride, and combinations thereof.

* * * * *